US007555425B2

(12) United States Patent
Oon

(10) Patent No.: US 7,555,425 B2
(45) Date of Patent: Jun. 30, 2009

(54) SYSTEM AND METHOD OF IMPROVED RECORDING OF MEDICAL TRANSACTIONS

(76) Inventor: Yeong K. Oon, 29 Darryl Street, Scoresby, VIC (AU) 3179

( * ) Notice: Subject to any disclaimer, the term of this patent is extended or adjusted under 35 U.S.C. 154(b) by 1018 days.

(21) Appl. No.: 10/491,933

(22) PCT Filed: Oct. 18, 2002

(86) PCT No.: PCT/AU02/01422

§ 371 (c)(1),
(2), (4) Date: Apr. 6, 2004

(87) PCT Pub. No.: WO03/034274

PCT Pub. Date: Apr. 24, 2003

(65) Prior Publication Data

US 2004/0249667 A1     Dec. 9, 2004

(30) Foreign Application Priority Data

| Oct. 18, 2001 | (AU) | PR8354 |
| Nov. 30, 2001 | (AU) | PR9225 |
| Apr. 17, 2002 | (AU) | PS1767 |
| Jun. 7, 2002 | (AU) | PS2844 |
| Sep. 5, 2002 | (AU) | 2002951382 |

(51) Int. Cl.
  G06F 17/27     (2006.01)
  G10L 11/00     (2006.01)
  G06Q 50/00     (2006.01)

(52) U.S. Cl. ................ 704/9; 704/270; 705/2

(58) Field of Classification Search ........... None
See application file for complete search history.

(56) References Cited

U.S. PATENT DOCUMENTS 5,331,554 A * 7/1994 Graham .................. 707/5

(Continued)

FOREIGN PATENT DOCUMENTS

GB         2327133         1/1999

(Continued)

OTHER PUBLICATIONS

Rachlin et al., "Accounting and Financial Fundamentals for Nonfinancial Executives", AMACOM, New York, 1996, pp. 1-13.*

*Primary Examiner*—David R Hudspeth
*Assistant Examiner*—Brian L Albertalli
(74) *Attorney, Agent, or Firm*—Fenwick & West LLP

(57) ABSTRACT

This invention relates to the field of patient health care. In particular, it relates to medical informatics, and to systems and methods for recording medical transactions. A system for recording medical transactions is disclosed, the system comprising distinct and multi-linguistic representation layers, allowing the de novo composition and construction of medical transaction codes; including a user interface including means for inputting medical transactions in a semiotic form one, the semiotic form one input being a free form-type, abbreviation-oriented natural language textual input, a transaction parser-coder configured to parse said semiotic form one input and to convert it into coded medical transactions in a semiotic form two output, the transaction codes composed and constructed de novo, the semiotic form two output embodying high level machine-parseable computer language statements comprehensible to a high certainty level by human users, means for evoking a display of system reflection in the form of coded medical transactions in said semiotic form two and system-rated confidence levels representing the match between a code and correspondence with perceived user intent, means for receiving user selection input for verifying a selected coded medical transaction, and a transaction mapper configured to convert a semiotic form two input into a semiotic form three transaction by mapping the selected coded transaction into data row in a relational database to render the transaction data amenable to structured query language processing. There is further disclosed a computer-based method for the management of medical transactions, including storing each medical transaction as a transaction code in a data row in a database table, each transaction code including a genre key relating to the nature of the transaction, and including providing storage ledgers for each genre, such that each transaction can be retrieved and displayed as an entry in a storage ledger in accordance with its genre key. This allows medical transactions to be treated akin to accounting transactions, signifying credits and debits in defined transaction ledgers.

34 Claims, 11 Drawing Sheets

U.S. PATENT DOCUMENTS

Figure 1:
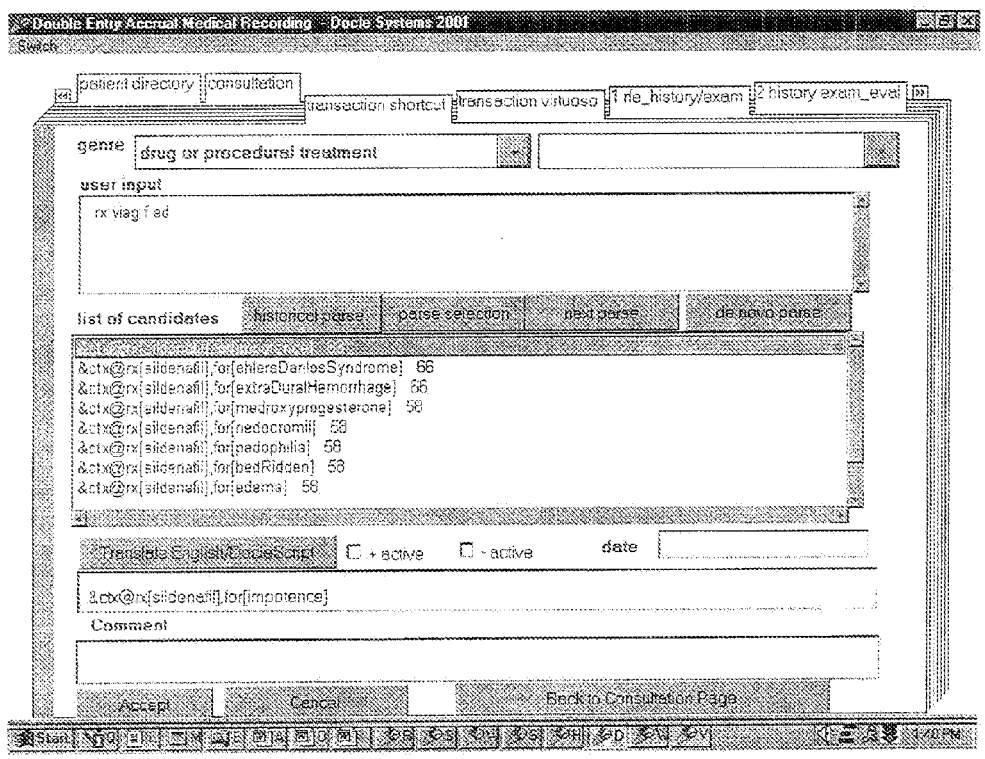

| | | | |
|---|---|---|---|
| 5,369,575 A * | 11/1994 | Lamberti et al. | 704/9 |
| 5,664,109 A | 9/1997 | Johnson et al. | |
| 5,832,450 A | 11/1998 | Myers et al. | |
| 6,182,029 B1 | 1/2001 | Friedman | |
| 6,915,254 B1 * | 7/2005 | Heinze et al. | 704/9 |
| 7,356,460 B1 * | 4/2008 | Kennedy et al. | 704/9 |

FOREIGN PATENT DOCUMENTS

| | | |
|---|---|---|
| WO | WO 99/17223 | 4/1999 |
| WO | WO 00/65485 | 2/2000 |
| WO | WO 00/14652 | 3/2000 |
| WO | WO 01/53987 | 7/2001 |

\* cited by examiner

SYSTEM AND METHOD OF IMPROVED RECORDING OF MEDICAL TRANSACTIONS

FIELD OF THE INVENTION

This invention relates to the field of patient health care. In particular, it relates to medical informatics, and to systems and methods for recording medical transactions.

BACKGROUND OF THE INVENTION

In this specification, where a document, act or item of knowledge is referred to or discussed, this reference or discussion is not an admission that the document, act or item of knowledge or any combination thereof was at the priority date:
(i) part of common general knowledge; or
(ii) known to be relevant to an attempt to solve any problem with which this specification is concerned.

Healthcare can be likened to a road trip with flat tyre stories that are constantly told and retold, this retelling being complicated by the fact that in the machine age these same stories have to be retold to both humans and machines. In the prior art, medical stories can be told in the form of (a) doctors' scribble and b) word processing in English, both of which are not computable in any appropriate integrated manner, in the sense that data processing of word processed documents and handwritten notes are not yet reliable. Medical computer record systems known from the prior art generally have considerable difficulty in encoding an entire medical history, and therefore only partial segments of the patient record are coded. Clinical coding is a time-consuming and highly skilled process.

The most efficient approach for the telling and retelling of these medical stories among a plurality of men and machines is with a language that is comprehensible to both humans and to machines. But healthcare workers have neither the time nor the training to interface with a computer system in a high-level computer programming language. The problem of medical story telling and retelling (among the interfaces of man-man, man-machine, machine-machine and finally machine-man) therefore persists.

SUMMARY OF THE INVENTION

The invention provides systems and methods for recording medical transactions as defined in the appended claims.

The invention addresses the drawbacks of known approaches through the use of distinct multi-linguistic levels of representation of the medical transactions, with de novo synthesis of coded transactions in various semiotic forms. The various levels and their different interfaces impose different linguistic requirements, and optimal semiotic solution being selected for each level.

Through the compositional nature of the transactional coding process, utilising input in the language of semiotic form one, effectively unbounded coding space can be generated.

The system reflection of user intent relates to the human readable coded transactions composed and constructed de novo, preferably ranked in probability of match, with subsequent user selection to provide verification of suitability of code in this mission-critical environment.

The invention thus provides a medical recording system and method based on distinct and multi-semiotic forms of representation of genre-specific medical transactions composed and constructed de novo via a medical transaction parser/coder, from abbreviation-oriented, misspelling-tolerant natural language-like input, enabling the storage, analysis and viewing of these transactions in debit- and credit-type ledgers, with transaction accrual functionality, as well as a method and means for sharing, processing and synchronising of localised and distributed medical records. Potentially, the invention provides a unified model of medical record informatics.

In this specification and claims, the following definitions are given:

Sentence—a group of words that express a complete thought, equivalent in this context to a 'medical transaction'.

Clause—a group of words that contain a subject and predicate.

Predicate—provides information about the subject.

Semiotics—the study of signs and sign-using behaviour, including the use of words, of tone of voice, tempo, or drawl or any paralinguistic features, of body motions and gestures and animal communication. Semiotics comprises pragmatics, semantics and syntax, and deals with the relationship between signs or linguistic expressions and their users. In linguistics, semiotics are broadly concerned with the relationship of sentences to the environment in which they occur.

Semantics—study of meaning, emphasizing the relationship between signs or words and their referents and including such concerns as naming, denotation, connotation and truth.

Syntax—the branch of grammar dealing with the way words are put together to make well-formed sentences.

Script—a text base for communicating structure and commands for machines.

DETAILED DESCRIPTION OF THE INVENTION

The applicant and inventor of the present application has previously developed a medical scripting language referred to generally as 'DocleScript', and described in applications WO 97/48059, WO 98/44432, WO 00/14652 and WO 01/39037, the contents of which are incorporated herein by reference. The present invention can be seen as a significant enhancement to the value and functionality of DocleScript, and the following description refers in part to the use of DocleScript. However, it is to be understood that the present invention is not limited to any specific form of application.

Prior art methods and systems do not address a number of problems:

1. The Problem of Clinical Coding Effort at the User Interface Level

A 'pick list' of disease codes is the usual way to code for a list of patient active problems. The user types in the first few characters and a pick list dynamically changes to present the entity that the user wants to code for.

This system is workable if the clinical codes are very limited. However, to code for a consultation with a patient presenting with half a dozen symptoms, half a dozen clinical findings on examination, a differential diagnosis of three diseases, four laboratory tests and a number of prescribed medications, would take so much time that the user is unlikely to choose to code for the whole consultation.

Prior art coding systems tend to a code reference for all concepts, some systems claiming to have enumerated codes for around 400,000 clinical concepts. Locating the right code can be akin to looking for a needle in a haystack.

The need therefore remains to provide a system to code for medical records that is as efficient (or more efficient) as doctor scribble. Doctors scribble on their notes short messages, such as: bp 120/80, T 38, P 78 reg, fever cough 2/7, no rash. warf for dvt. sild f ed. This can be translated by clinicians as: blood pressure 120/80, the patient has a fever of 38 degrees centigrade and pulse of 78 regular, and has had a cough for 2 days but has not got a rash. Warfarin is given for deep vein thrombosis, and Sildenafil is prescribed for erectile dysfunction. The task, then, is to convert these scribbles into precise structured computer language that the machine can code, store and process.

2. The Problem of a Plurality of Coding Systems

There exist in the world disparate medical coding systems, representing different coding paradigms, including ICD9, ICD 10, ICPC, ICPC-PLUS, Docle, Snomed-CT. Different groups use different ones of these various coding systems, each coding system having its supporters. It is frequently important to exchange information across applications that use the different coding system. One way out to accomplish this is to use maps, but mapping from one system to another is fraught with pitfalls, as the accuracy of the information deteriorates as it moves from one map to other. The problem is akin to a message that is whispered sequentially down a line; in very few steps the veracity of the message is likely to deteriorate significantly.

The invention tackles this issue by basing the disparate coding system on Namespace-Tertiary keys, with associated components of namespace, relationship operator, and semiotic form two native code.

3. The Problem of Coding for Medical Transactions—the Doctor/Machine Interface

Medical codes are conventionally enumerated into a pick list, but these standalone codes are devoid of contextual possibilities. For example, there is a code for diabetes mellitus, but there is no code to depict 'no diabetes' or 'diabetes from pancreatitis and obesity'. In prior art coding systems, for every clinical situation, there is a reference code already enumerated.

So a code would exist for the scenario of: fever, cough but no rash. There will be yet another code for the scenario: cough but no rash, and still another code for the scenario: fever, cough, diarrhoea but no rash. This enumerated scenario typically means that the user has to select the right code from a pick list comprising of hundreds of thousands of already enumerated items. In prior art system, the enumerated items are either signs or symptoms or diseases or drugs or procedures. Because the process of medical recording in real life is transactional (that is, in paper recording a clinician records symptoms, signs, assessment and plan in a constant flow manner), computer encoding of the whole consultation as a series of medical transactions using the system of enumerated pick lists is tedious at the user-machine interface. The time-consuming nature of coding means that medical history and examination notes in prior art medical systems are not coded, only critical segments of medical records such as allergies, current medications and active problems are coded. Yet medical decision support demands that every aspect of history and examination during the medical encounter be coded, otherwise it is not possible for the system to comprehensively provide the machine cognitive services needed to properly augment the clinician's level of medical care.

Some of the technical difficulties in implementing of a user-composable medical transaction coding system include the following:

a) location and specification of a medical context genre for the transaction, be it reason for encounter, history or examination, evaluation, management, etc;

b) finding a context genre with the right attributes eg. in the transaction coding of, say, a drug treatment for a disease, the user needs to grapple with the field for the drug and the field for the disease. This problem becomes critical when there are multiple fields, such as in a pharmaceutical prescription, where there are fields for drug name, trade name of drug, dose, frequency, pack size, repeat and special instructions;

c) the user needs to move from said field to field, and at each field will need to open a pick list, enter a search string to bring up candidates, and scroll and select to populate one field at a time;

d) the system needs to parse the end result for well-formedness, and then store transaction in a table with the correct column attributes.

Take the example for coding the fact that Sildenafil is prescribed for erectile dysfunction in a patient. In a conventional system, the user has to constantly change mode: entering patient notes mode, switch to panel to get list of symptoms, select symptoms, select duration mode, set the value, switch back to physical examination mode, etc. The time-consuming process of medical coding means that only specific sections of the medical record are coded, typically list of diagnoses, drugs and known allergies.

In this embodiment of the present invention, referred to herein as 'DocleTalk', an efficient free natural language termed semiotic form one is provided. This presents a solution to this doctor/machine bottleneck.

4. The Problem of Needing to Code for an Unlimited Array of Constantly Changing Clinical Scenarios The user/medical record interface problem in coding for every step of the healthcare process extends to the problem of motivated patients who wish to keep their own medical record. With the paradigm shift of better-informed and proactive patient outlooks, the patient can be empowered to take charge of their own healthcare, once they learn how to encode their own medical record. This encoded medical record can then be sent over the Internet or carried in portable media for digital processing and evaluation. The incentive to keep one's personal record generates initiatives, such as tracking blood pressure, glucose and cholesterol levels.

5. The Technical Problem of Unique Patient ID Number

The patient in a modern society has ample access to a multitude of care providers, which may comprise several family doctors, several pathology and radiological laboratories and several medical specialists. Healthcare is expensive and duplications of tests, drugs, procedures and sequestration of patient health data by individual healthcare provider will inevitably lead to wastage and sub-optimal care. Synchronisation of distributed medical data can only be promoted by a unique patient identifier, but unfortunately each health care provider generates its own unique identifier and has its own method of transactional representation. At each site of care, recording of patient data occurs, this data being usually stored in a computer database. At each site, data pertaining to a particular patient is assigned a unique patient identifier that is unique to that particular healthcare organization. Healthcare in the 21st century is about universalisation, collaboration, aggregation and translation of medical data pertaining to a particular patient across all geographical and care-provider boundaries—to make the health data available anywhere at any time to accredited care providers. A significant problem, then, is the lack of a provider-verifiable universal patient identifier for tagging transactions, to which the proliferation of Medicare care card numbers bears testament.

The government in Australia, as in other jurisdictions, is unwilling or unable to introduce a nationwide unique patient identifier for the specific purpose of transportability of partial or whole medical records/transactions across the various healthcare sectors. The Docle coding system, based on the biological Linnean classification system, is the most widely used coding system in general practice in Australia. The Docle paradigm acts a powerful filter for problem solving in this particular domain. The present invention includes a system and method of patient unique identifiers based on Linnean Classification and Namespaces—which can be supervised by the various general practitioner divisions under the auspices of the ADGP—forms the foundational backbone for an effective de facto national unique patient ID system.

6. The Problem of Managing Medical Record Views and Notarising for Tamper—Proofing Modern healthcare is complex in terms of information flow. The prior art utilises posting of health data into collections or lists, these lists including the medications list, the problem list, the consultation list, the patient review list, the list of tests, the list of test results. There is no common framework around the posting of the medical transactions. There are requirements for storing the information in such a manner that the patient status can be quickly abstracted, and that the items of information stored are logically linked to one another. For example, a medication must be linked to the reason for prescribing; a test must be linked to its test results; a test must be linked to differential diagnosis or diagnoses; a planning goal must be linked to a procedure or a treatment. The associated problem is the veracity of the medical record. The present invention makes it possible to view patient data in a manner analogous to the way in which an accountant views his ledgers, and makes medical records less prone to tampering, by affording ready detection and discouragement of altered transactions and deletions of transactions.

7. The Problem of Remoting Medical Transactions

The paradigm of medical records and notes sitting tight on a desktop, or merely connected to a LAN, is considered too limiting for a 'connected' vision of healthcare for the future. Patient clinical and drug data must be moved across boundaries in a timely, seamless fashion. These boundaries relate to issues including geography, computer process, computer applications, and computer objects running in the same or different machines connected by way of a LAN or Internet. The prior art does not provide a solution that is both platform- and application-independent. The present invention aims to provide an open and transparent system, amenable to inspection and reflection, so that software developers can comment on and suggest improvements on the model. This solution leverages on state of the art database and internet standards or emerging standards such as XML, HTTP Sockets, email, web services and SOAP (Simple Object Access Protocol) that transcend both .Net and non-.Net functionalities.

The concept of moving this data object (which may be a drug prescription or reason for prescribing, a reason for encounter, symptoms, signs, diagnoses, management, clinical plans or goals) is referred to as 'remoting'. The process of getting this object ready is referred to as 'marshalling'. Even on a single machine, the data object must be moved across contextual, application and process boundaries. Remoting an object is akin to beaming up Scotty in Star Trek. For successful remoting, 'sinks' or enforcers are required at both ends, to ensure that the message gets through. In the Star Trek analogy, the language for communication is Federation Standard, if Captain Kirk speaks in Vulcan, the formatter automatically converts it to Federation Standard before the message is sent down the channel.

In the embodiment of the invention, the health message contents are standardized on a high level computer language, DocleScript, this being a unitary health language in the sense that the health codes and the internal contextual wrappers are seamless.

In the health data remoting approach of the invention, the details of the health transaction (which in this example is about a reason for encounter) is encoded in semiotic form two and held as a data object. For the purpose of remoting, this Data object containing the semiotic form two data is then marshalled and serialized into an XML file which can then be transported by a variety of channels, such as email, Internet request, floppy disc, memory stick, HTTP sockets, etc.

This XML file, which describes its own internal schema and data contents in semiotic form two, can then be read in and reinstantiated into a Data Object, which can then be manipulated, and decoded to other coding systems if required, and the user database can be updated.

The challenge is to avoid the use of English (or similar language) content in these messages, as English per se is of minimal value for data processing and analysis/decision support. The choice of semiotic form two is supported by the fact that semiotic form two is both human and computer readable. The solution of the invention is a disconnected architecture based on data objects encoded in semiotic form two. Such an architecture scales well, as does the analogous current paper model, keeping track of patient-health provider sessions as disconnected discrete sessions. The method of the invention provides a just-in-time connectedness, where disparate sessions can be seamlessly integrated by the importation of such data objects coded in semiotic form two.

The problem to be solved may be seen as analogous to the moving of chocolates from the chocolate factory to the consumer. The chocolates are medical data objects represented in semiotic form two (this is both human and computer readable). Now the chocolates have to be despatched to supermarket to be sold, hence the need to wrap these chocolates—which are of various flavours—in all sorts of brightly coloured wrappers (semiotic form two wrappers). In turn, these wrapped chocolates need to be packed in small boxes (XML) with titles such as "Golden Assorted Chocolates". In turn, these small boxes are packed in crates (XML and XML serializable Database objects) and dispatched through the road, air or rail system (the wrapped objects are channeled by email, floppy disk, or internet message, etc).

The consumer knows which chocolate to consume by inspecting the box of chocolates (XML schema) and the colour of the wrapper (semiotic form two Context Wrappers).

The following description of an embodiment of the invention is given by way of exemplification, and reference is made to the attached drawings, which represent screen shots from a computer application embodying the present invention, and which serve to clarify various features and advantages of the invention.

In these drawings,

FIG. 1 of 11—shows the transaction coder at work, semiotic one text is entered in input pane.

Figure 2:
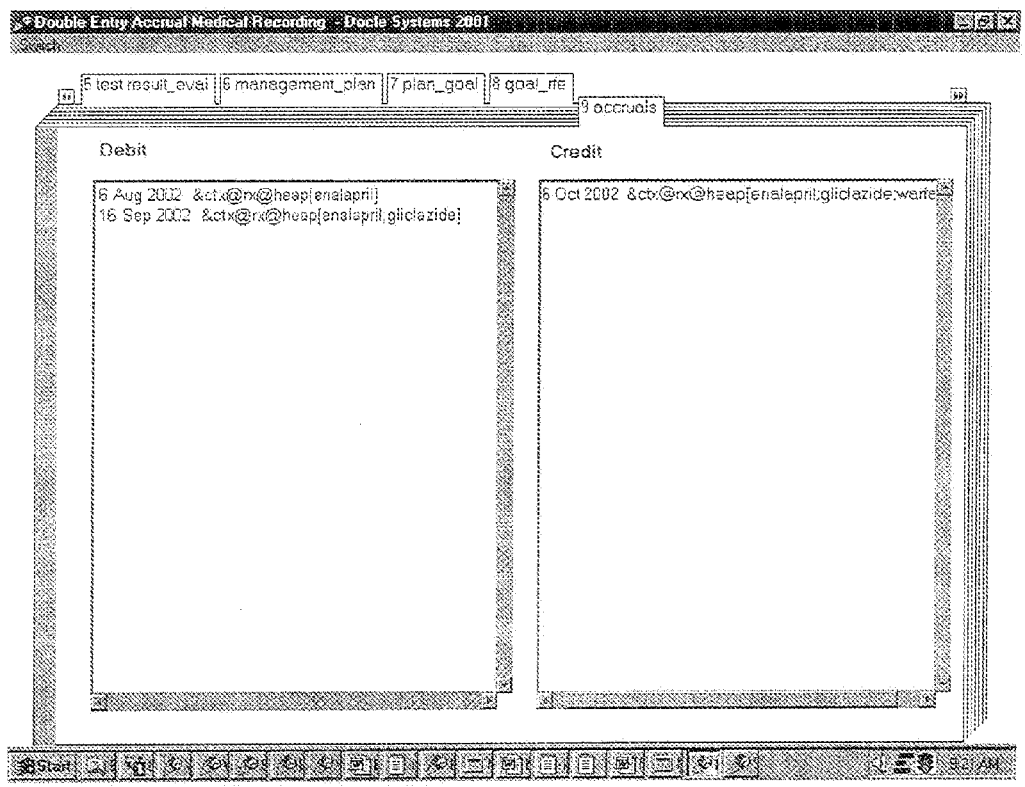

FIG. 2 of 11—shows the accruals ledger, the credit side shows latest heap transaction.

Figure 3:
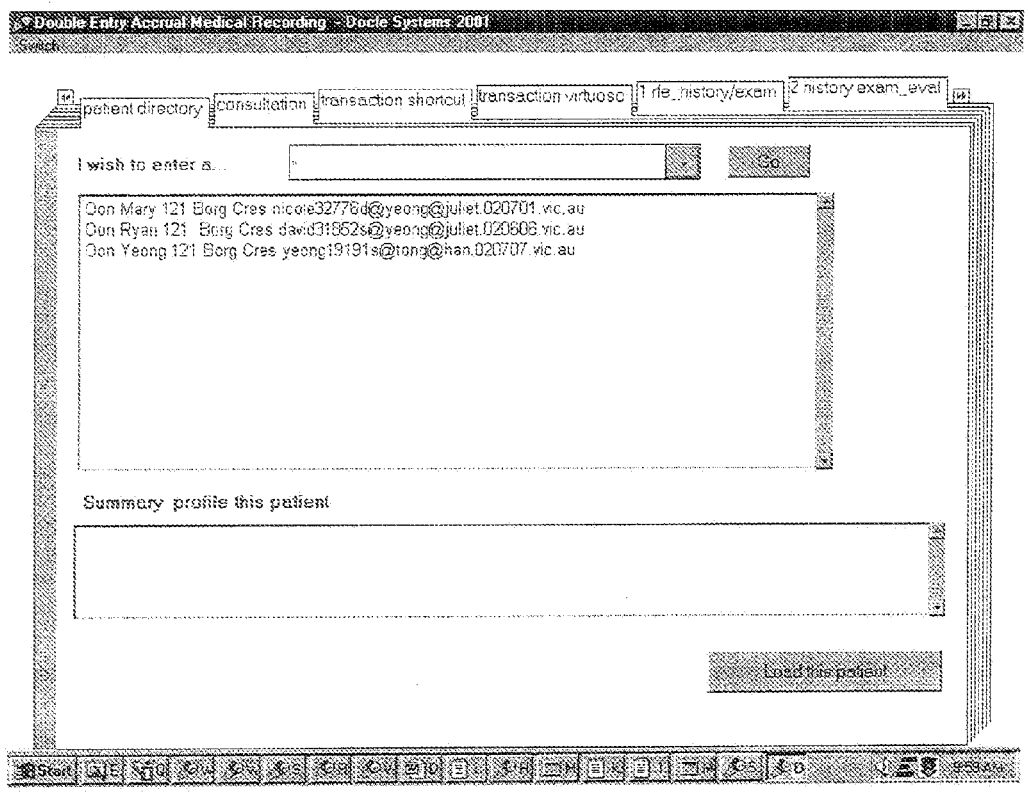

FIG. 3 of 11—shows the patient directory with linnean unique patient identifiers.

Figure 4:
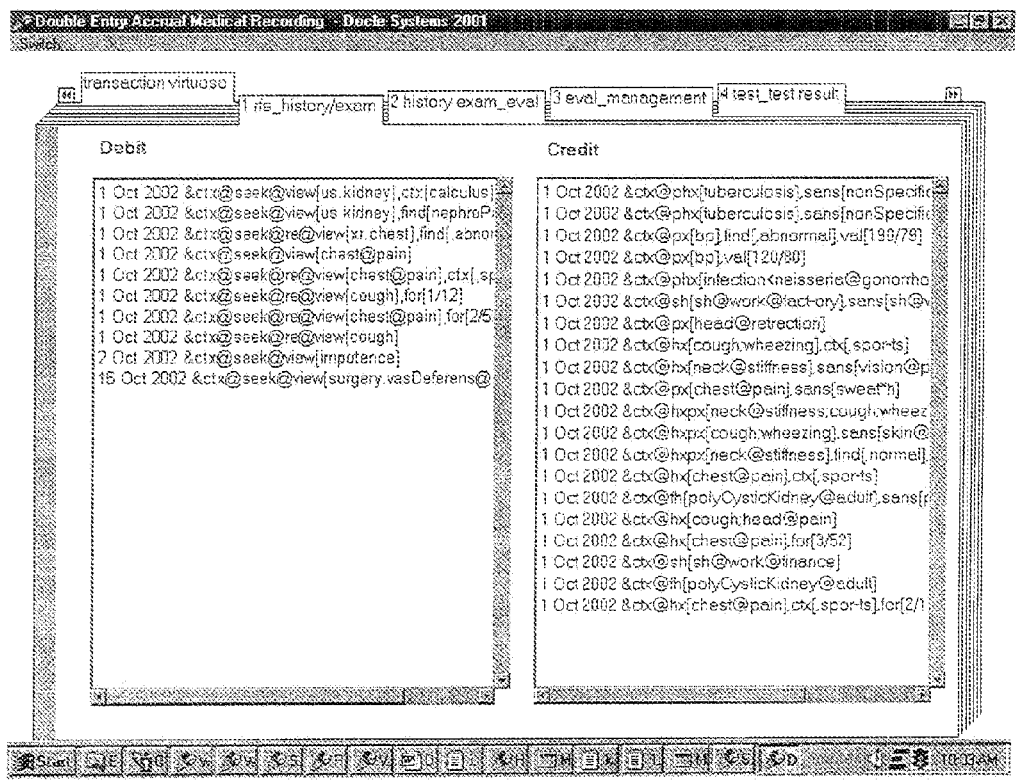

FIG. 4 of 11—shows the rfe (reason for encounter)—history/examination ledger.

Figure 5:
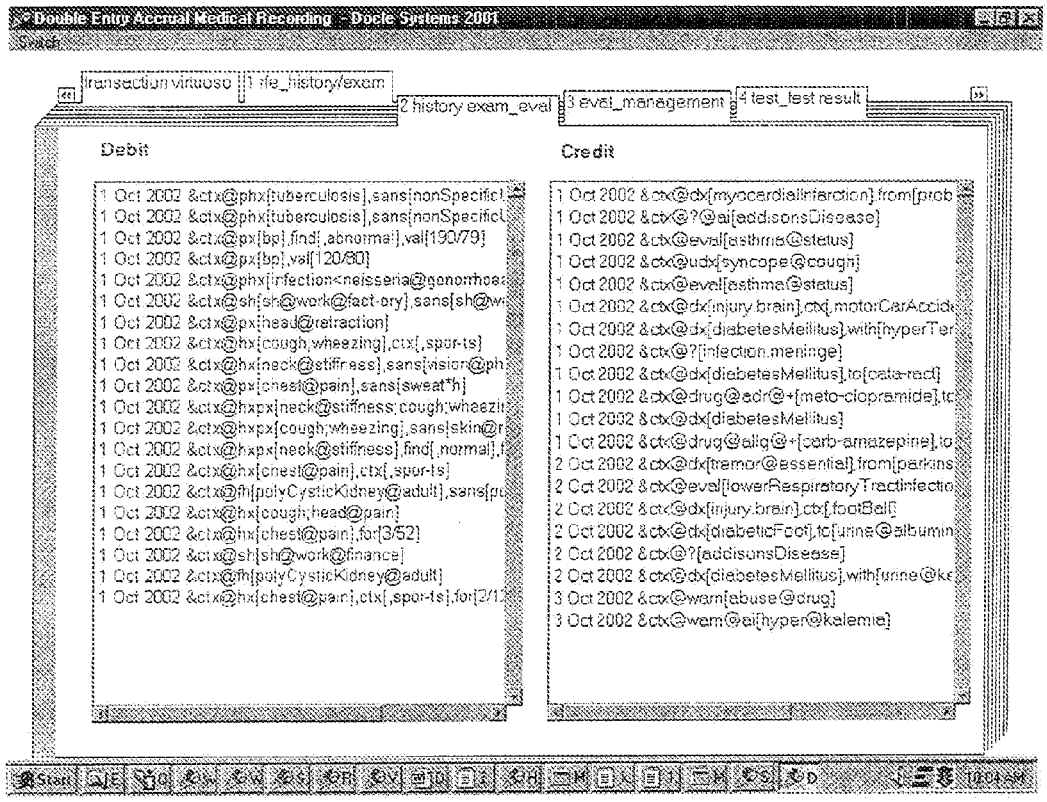
Figure 6:
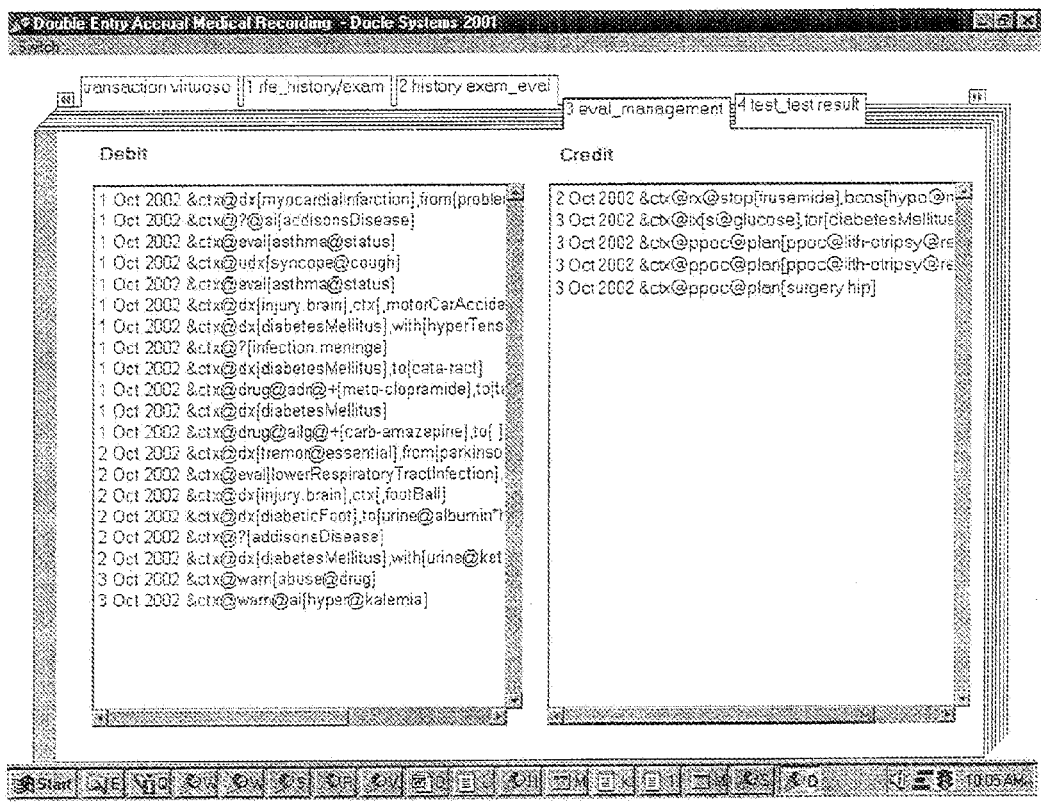
Figure 7:
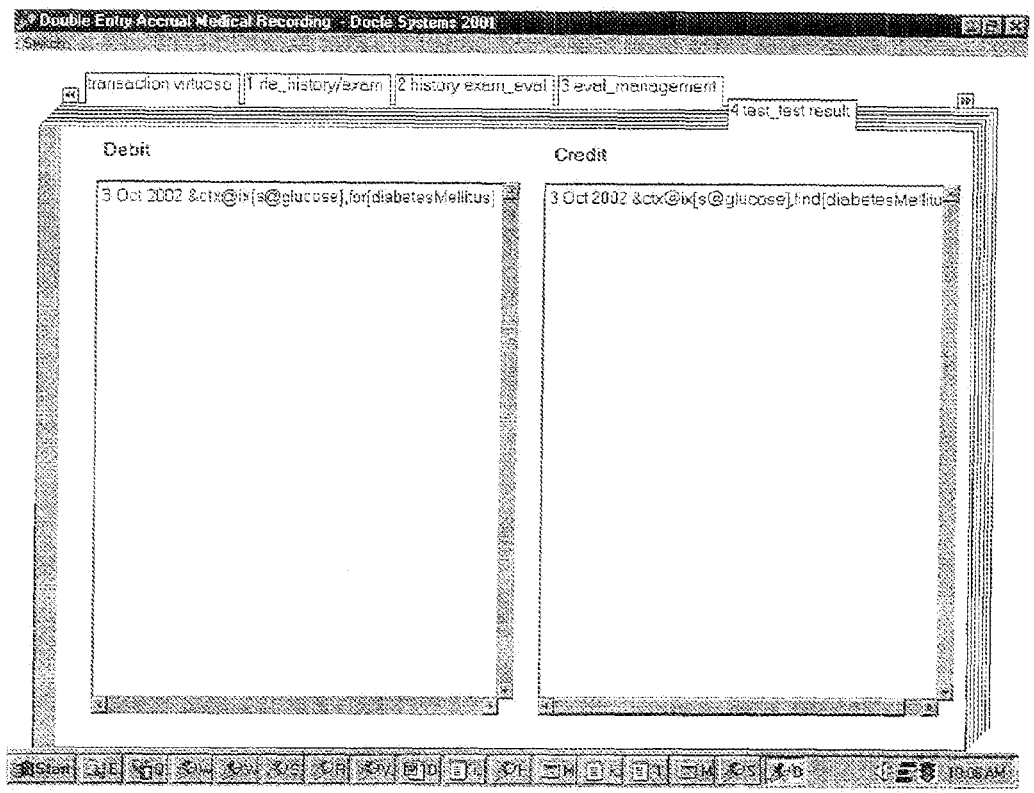
Figure 8:
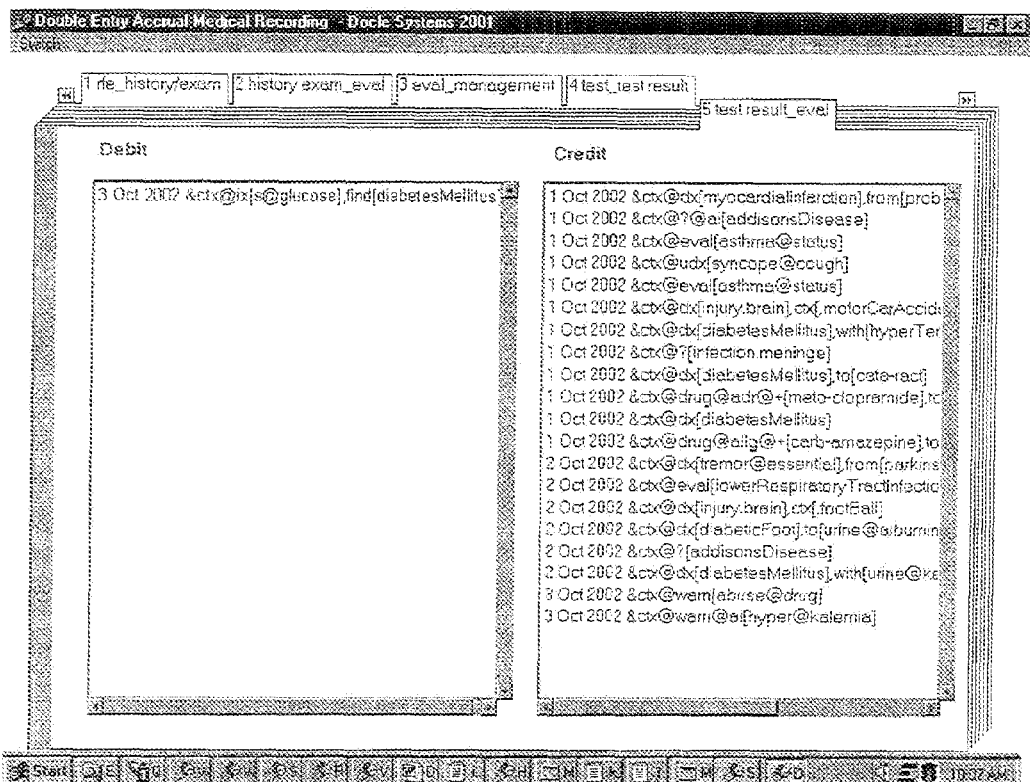
Figure 9:
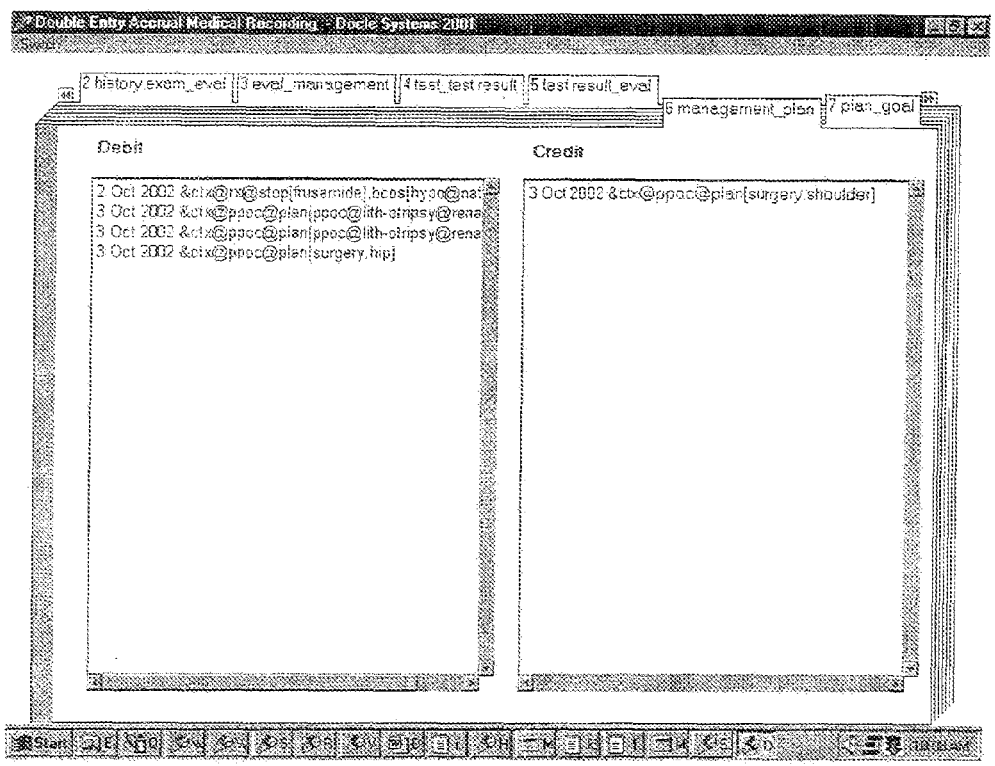
Figure 10:
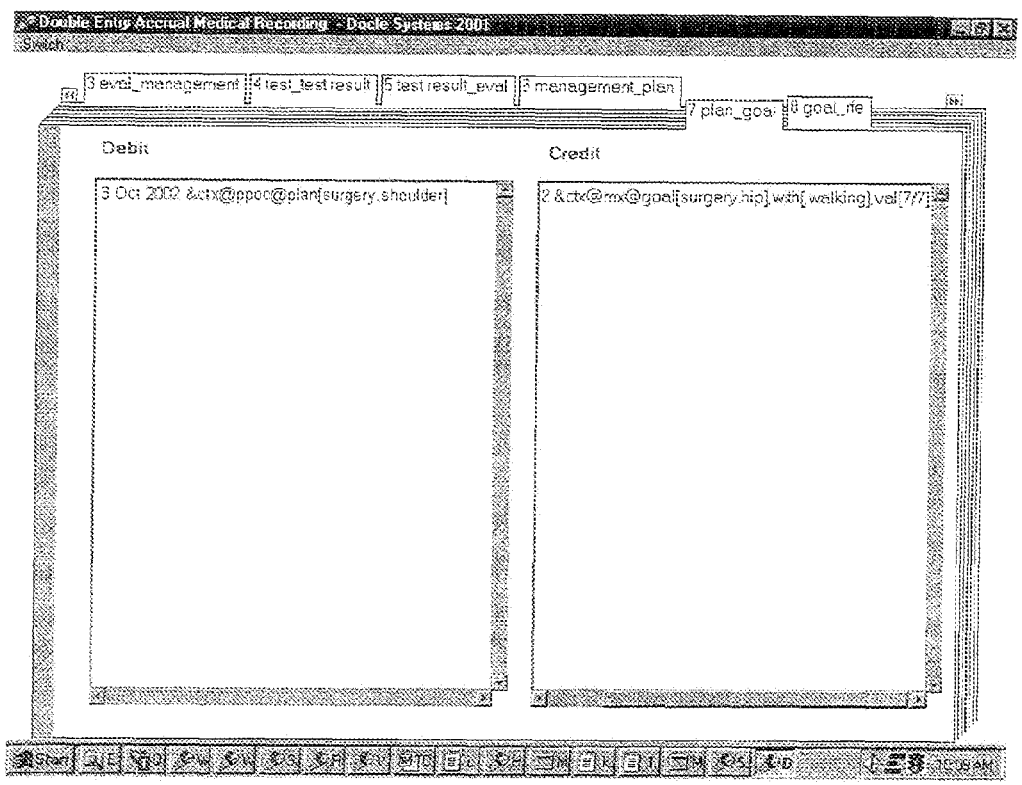
Figure 11:
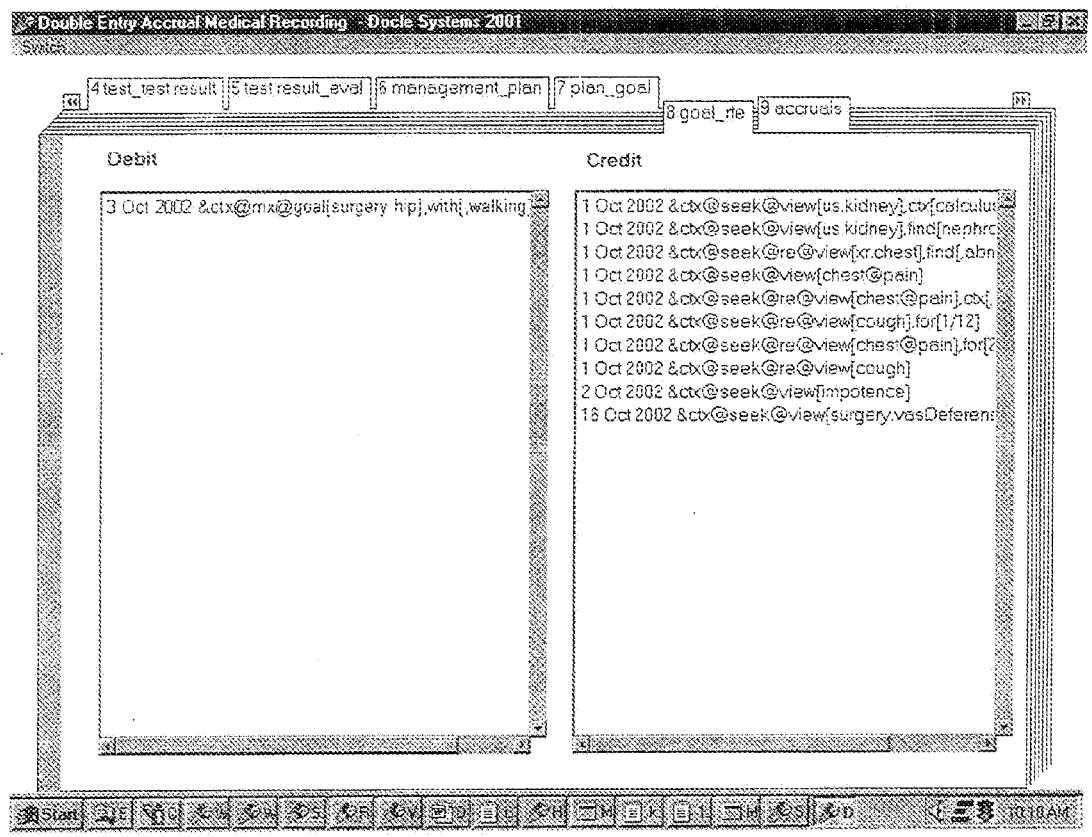

FIG. 5 of 11—shows the history/examination—evaluation ledger.
FIG. 6 of 11—shows the evaluation—management ledger.
FIG. 7 of 11—shows the test—test result ledger.
FIG. 8 of 11—shows the test result—evaluation ledger.
FIG. 9 of 11—shows the management-plan ledger.
FIG. 10 of 11—shows the plan—goal ledger.
FIG. 11 of 11—shows the goal—rfe (reason for encounter) ledger.

In this embodiment of the invention, the data representation of medical data is at four distinct linguistic layers, ranging from (a) a natural text-like level, termed semiotic form one (b) a computer high level language representation of health data, termed semiotic form two (c) health data held in computer high level language, placed into a data relation and made amenable to structured query language (SQL) operations, termed semiotic form three (d) medical data expressed in semiotic form two or three, and marked-up for transportability of data using SGML or XML.

The invention involves the definition and separation of the different abstraction levels into a plurality of linguistic levels. A plurality of distinct linguistic levels solves the problem of encoding, processing and sharing of medical records. The invention is based on natural language-like, abbreviation-intensive, misspelling-tolerant, free format input of the semiotic form one. The data input is transformed into several distinct linguistic layers suitable for data processing and decision support. In a preferred embodiment of the invention, the distinct semiotic forms comprise:

1. Semiotic form one (DocleTalk)—a method of efficiently communicating intended coded medical transactions using a free form text message, termed semiotic form one (Docle-Talk), which can be viewed as a formalized and very efficient doctor talk. This is used as the language for the health worker to input into the medical recording system. This context-sensitive, terseness-oriented language is based on system-mandated and individual user-defined abbreviations, predominantly of one to four letter words and contextual shortcuts, and leveraging on the clinician's own powerful understanding of the language of medicine. This enables a powerful and succinct way to communicate to the machine the user intent.

The vocabulary of the language in semiotic form two (see below) comprises medical terms that all have a standard form of abbreviation, typically the first four characters of single word expressions. In two word expressions, the abbreviation is the first four characters of the first word, plus the first character of the second word. In expressions of three or more words, the abbreviations are made up of the first character of each word of the expression. Hence fracture is denoted as frac while 'diabetes mellitus' is 'diabm'. Research has indicated that usage of these standard abbreviations provide a totally reliable system certainty of user intent. Through the coordination of the use of terse keyword anchors and mandated casts of allowable transactions (see below), the doctor interface language of semiotic form one can manage contextual relativity. The system is tolerant of spelling mistakes and computes the 'likeness' of each token along the way. For instance, the string 'iabm' is similar to the string 'diabm', the latter being the secondary key or standard abbreviation for diabetesMellitus. Typing diabm means that the system knows with 100 percent certainty that the user intended diabetes mellitus and diabetesMellitus only. Typing a string like 'iabm' will evoke an 80 percent confidence level that the user intended diabm (and thence diabetes mellitus). The key to the operation of doctor talk is that the clinical codes used are word-based. These primary keys have as their secondary keys an abbreviation that is computer algorithm generated. For example, diabetes mellitus is diabm, 'transient ischemic attack' is tia.

The user needs determine only the first four characters of a one-word expression (e.g. carcinoma is carc). For a two-word expression, the first of the two words is treated like a one-word term plus the first character of the second. Hence, 'herpes zoster' becomes herpz while 'herpes simplex' becomes herps. This recruitment of all secondary keys as part of the vocabulary for the semiotic form one of doctor talk gives rise to a very succint language, derived from the creation of these standard abbreviations, on top of any abbreviations that the user can use as shortcuts to the primary or secondary keywords. Thus, a minimal of keystrokes is required for highly objective input.

Semiotic form one can thus be seen as analogous to perfect and imperfect natural language scribble, typical of a clinician's handwritten notes in their paper medical records, with a heavy emphasis of one to four letter words. Examples of use and their interpretation in standard English, demonstrating the loose free form nature of the semiotic form one, include:

```
viag for ed    -> sildenafil for impotence
sild f ed      -> sildenafil for impotence
warf f dvt     -> warfarin for deep vein thrombosis
```

2. Semiotic form two (DocleScript)—the data expressed in semiotic form one is parsed into a computer high level language representation of the information held therein. The semiotic form two representation has its context genre and context species defined. The following two transactions are examples of semiotic form two that belong to the genre called genre@mx.

&ctx@rx@+[sildenafil],for[impotence],note[    ],auth[474603X],coda[ ]

&ctx@rx[warfarin],for[deepVenousThrombosis],note[ ],auth[474603X],coda[ ]

Note that each transaction has a subject (&ctx@rx, which signifies context treatment) and a series of predicates, as detailed in language definition below.

3. Semiotic form three (DocleSQL)—this is the language representation meaningful to database systems, in this case compatible with SQL (Structured Query Language) ready. The representation in semiotic form two is parsed and converted into a language representation that is held in a data row of a relation table with defined attributes, these attributes corresponding to the attribute-joiner of the transaction in semiotic form two. Semiotic form three is typically a row in an SQL table suitable for SQL manipulation and other computer processing. The transaction of semiotic form three has properties of reflection of the genre type of the transaction in the attribute referred to as 'genre' and the species of the transaction in the attribute referred to as 'cast'. The system need not parse the whole transaction to discern the nature of the transaction, but needs only scan the genre and cast attribute, in order to gain an understanding of the nature of the transaction. A semiotic form three representation has attributes/fields to store the actual representations held in semiotic forms one and two.

The following transaction example creates a semiotic form three data row in a transact relation table:

'INSERT INTO transact
  (patientId, dateEntry, dateEvent, genre, transactType, theme, docleScript, note, auth)

VALUES ("david31852s@george@julia.020606.vic.au", "2002/6/6", "2001/12/1", "rfe", "&ctx@seek@view [ ]", "abuse@diazepam", "&ctx@seek@view [abuse@diazepam]", "favourite son, "473633 x")'

In the above example the context genre is "rfe" while the exoskeletal cast is "&ctx@seek@view[ ]".

4. Semiotic form four (DocleFS)—this is the transport or import/export representation layer. This layer enables the coded information plus the original input in semiotic form one to be exported to another database table. A transaction in semiotic form four can be reconstructed back to any of semiotic forms one to three. There are a number of variants or dialects of semantic form four:

a) marked up in SGML/XML, or any markup language of the data row in XLSLT and XML,
 b) as in an SQL statement, constructing the data row,
 c) a transaction in semiotic form two can be marked up,
 d) the data row with table attributes can be marked up with special delimiting characters and sent.

The method of the invention therefore affords encoding for part of or for the entire medical encounter, suitable for presentation as a ledger of transactions and suitable for computer processing based on natural language type input of semiotic form one. This involves:

1) converting perfect and imperfectly spelled, correct or incorrect grammar, natural language-type abbreviation-oriented text into transactions (semiotic form one), by splitting a natural language text chunk into smaller transaction text chunks using a transaction splitter,
 2) converting each imperfect natural language transaction text chunk into a high level language (semiotic form two) using a transaction code parser,
 3) converting each semiotic form two transaction into a data row (semiotic form three) using a high level language-to-data row converter (semiotic form two-semiotic form three converter). These transactions are suitable for presentation as real or virtual double entry ledgers with accrual transactions in an accrual table (see below),
 4) inserting a transaction of semiotic form three in one or more transaction tables, which may be distributed in one or more computers,
 5) transferring of each data row to SGML (semiotic form four) using XLST/XML or as an SQL instruction for export of a data row,
 6) optionally moving backwards in the semiotic form chain, ie restoring original semiotic form,
 7) allowing, along the chain, user direct visual verification of the veracity of the actual machine coding translations/output.

The invention also comprehends an approach of double entry of medical transaction recording. This is an improved system and method of computerized medical recording based on the genre types of transactions in healthcare, these transactions being collected in a journal, and then entered utilising a double entry method into ledgers. A double entry transaction entails a transaction posted in the debit column of one ledger, and the same transaction posted in the credit column of another ledger. This double entry method is a solution to the problem of keeping track of the multitudinous informational demands of modern patient care. As certain transactions can be flagged to generate a plurality of other transactions, this method is ideally suited for pre-emptive style of health care suited for preventive health action and minimisation of health litigation that may arise from omission on the part of the health provider. This recording system enables a true clinical picture of the patient to be abstracted from a clinical record and is designed around planning and goal-oriented patient care. Each transaction in the journal and ledgers are subjected to a hash function, which produces a running checksum balance after each transaction. These hash balances are computed into a medical record checksum, which is expressly disseminated outside the medical record environment, and in the course of normal clinical practice, the checksums held outside the record environment serve to verify the integrity of the medical record.

This approach can be regarded as a 'double entry' medical bookkeeping method, which provides a range of functionality, including addressing the following:

1) The current value or status of a patient's health, based on the concept of informational assets,
 2) The change in value or status of a patient's health over a given period of time, this component referred to as the 'health delta',
 3) Logical links between each transaction of health data to its logical connection, based on the concept of informational expectation and informational denouement,
 4) Autogeneration of planning goals,
 5) Facilitation of patient management, by evaluating for unfulfilled expectation in the ledger columns of the patient record.

Doctors, nurses, investigators and allied health personnel require complete health information for improved decision-making. In this embodiment of the invention, an individual patient medical record is kept in computerized books, and the patient health can be seen as analogous to the account data of a corporation. There are two types of books used in medical double entry bookkeeping; the journal book and the ledger books, which in the preferred embodiment are dynamically created as each patient's data is viewed. A journal can be a database table, comprising the day-to-day transactions (presentation and reason for encounters, investigations, test results, differential diagnosis/diagnosis/problem formulation, treatment, planning and planning goals). Each of these transactions is like an entry into a journal, and each transaction is debited and credited into two separate ledgers when the patient record is viewed.

From these ledgers, it is possible to get a monthly (or at any chosen interval) evaluation of the health delta or change in the patient health status. From these ledgers, it is also possible to get a balance sheet of the patient's health; this balance sheet comprising information on:

1) the health requirements and expectations of the patient,
 2) medical responses to (1),
 3) the health worker's expectations, based on the management of the patient,
 4) health planning and planning goals for (3).

The components of the system are essentially informational:

1) Expectation—Expectation can be on the part of the patient or the doctor.
 2) Denouement—Denouement satisfies the particular expectation.

Each transaction is entered into a table and double entry transactions become a debit in one ledger and a credit in another ledger when the patient data is inspected. A debit is a transaction that encapsulates a packet of 'expectation' on the part of the patient or the doctor, whilst a credit is a transaction that encapsulates a packet of 'denouement' for the patient or the doctor.

A transaction that is a denouement in one ledger is automatically transformed into an expectation in another ledger.

Each credit creates an 'instance' of a counterbalancing debit in another ledger, and each debit creates an 'instance' of a counterbalancing credit in another ledger.

Each transaction is thus perceived as doubly entered, one entry on the debit side of one ledger, and an identical transaction on the credit side of another ledger. Each ledger has an transaction balance and an accrual balance.

A transaction that carries a stigma of "@+" leads to an additive updating of the accrual transaction balance.

A transaction that carries a stigma of a "@–" leads to a subtractive updating of the accrual transaction balance.

A transaction that carries a stigma of a "@vary" leads to an updating of the accrual balance of each ledger, with updating of an element of a heap.

An accrual balance transaction has the stigma "@heap".

General Rules for Posting Transactions

Debit the ledger account that received value that is expectational.

Credit the ledger account that is receiving value that is denouementary.

Debit the medical asset ledgers for transactions that give value to the status.

Credit the medical asset ledgers for transactions that 'explain' the test results.

This latter transaction is then posted onto the 'nominal account' of 'problem List', which itself comprises diagnosis and 'problemFormulation'.

In addition, if a transaction is an accrual transaction, it is stigmatised by: '@+' '@–' '@vary' (see above), and the heap transaction is then updated in the accrual ledger, a new heap transaction being posted in the credit side of the accrual ledger and the old heap transaction being moved to the debit side of the accrual ledger.

From these operations, the system is readily able to extract the active disease, the active drug and other active patient status lists.

The Ledgers

Every transaction is posted into a table of transactions and, when viewed, posted into the debit column of one ledger, and immediately, posted into the credit column of another ledger. The ledgers are, in the preferred embodiment the following eight plus the accrual ledger:

1) rfe—history/exam
2) history/exam—eval
3) eval—management
4) test—test result
5) test result—eval
6) management—plan
7) plan—goal
8) goal—rfe 1. rfe (Reason for Encounter)—History/Exam Ledger On the credit side are the transactions with genre 'reason for encounter'.

On the credit side are transactions of the history and physical examination genre type.

An example of a debit: &ctx@seek@view[tiredness; weight@loss]

An example of a credit: &ctx@px[chest@examination], find[chest@rales], sans[wheezing]

2. History Examination—Evaluation Ledger

This ledger involves history/examination which comprises symptoms and signs on the debit side. On the credit side of this ledger are the differential diagnosis/diagnosis/evaluation of the problem.

An example of a debit: &ctx@hx[tiredness;thirst*h; weight@loss],for[2/12]

An example of a credit: &ctx@ddx[diabetesMellitus;upperRespiratoryTractInfection]

3. Evaluation—Management Ledger

This ledger involves evaluation comprising diagnosis, differential diagnoses and evaluations on the debit side. On the credit side of this ledger are the management of the problem.

An example of debit: &ctx@ddx[diabetesMellitus;upperRespiratoryTractInfection]

An example of credit: &ctx@?[diabetesMellitus:upperRespiratoryTractInfection]

Or: &ctx@rx[gliclazide], for[diabetesMellitus]

4. Test—Test Results Ledger

This ledger involves diagnostic imaging and diagnostic non-imaging tests on the debit side. On the credit side of this ledger are the findings of these tests.

An example of debit: &ctx@ix@[glucoseToleranceTest], for[diabetesMellitus]

An example of credit: &ctx@ix@with[glucoseToleranceTest],find[diabetesMellitus]

5. Test Result—Evaluation Ledger

This ledger takes test results on the debit side and evaluation on the credit side. The debit transaction in this ledger is also posted to test—test result ledger as a credit transaction. For the diagnosis/evaluation transaction of, say, diabetes mellitus, which can be automatically generated on meeting the condition of abnormal glucose tolerance test, the diagnosis is entered into the credit side of this ledger and a corresponding debit entry entered into the evaluation—management ledger.

Each test has an attribute to indicate belonging to a certain physiological/pathological class. Hence a series of virtual ledgers, each associated with a particular pathophysiological system, such as 'perinatal' 'trauma' 'adolescentHealth' 'geriatric' 'iatrogenic' 'blood' 'infective' 'congenital' 'medicalEmergencies' 'toxicologic' 'genetic' 'dermatologic' 'genitourinary' 'gastroIntestinal' 'fluidBalance' 'hepaticBiliary' 'opthalmologic' 'neoplastic' 'otolaryngologic' 'musculoSkeletal' 'respiratory' 'metabolic' 'cardiovascular' 'dentalOral' 'nutritional' 'immunologic' 'femaleHealth' 'substanceAbuse' 'mental' 'reproductive' 'maleHealth' 'physicalEnvironmental' 'pediatric' 'renal' 'nervous' 'skin' 'nuclearMedicine' 'unclassified' 'endocrine' will give a 'trial balance' picture of the patient health status as evinced by these tests results. An example of debit:

&ctx@ix[glucoseToleranceTest]],find[,abnormal,high; diabetesMellitus]

An example of credit: &ctx@dx[diabetesMellitus]

6. Management—Plan Ledger

This ledger takes management on the debit side and management plan on the credit side. The debit transaction is posted from a ledger with a credit transaction, in this instance from the plan-goal ledger. The clinician makes the decision to start this patient on a medication called gliclazide for treatment of the diabetes mellitus. A corresponding transaction is posted on the credit side of the evaluation—management ledger.

Viewing this ledger account would clearly illustrate the list of problems this patient has and the associated treatments. Note also that the treatment details are formulated in a non specific manner with no mention of doses. Detailed description of a prescription is listed under management plan. So on this ledger on the debit side one would see information as shown in the following example:

An example of debit: &ctx@rx[gliclazide],for[diabetesMellitus]

An example of credit:

&ctx@rx@plan@+[gliclazide],tn[Diamicron],dose[80 mg],qty[1],freq[bd],pack[100],rpt[5]

7. Plan—Goal Ledger

This ledger takes management plan on the debit side and management goal on the credit side. The debit transaction that is posted here entails a credit transaction on the management—plan ledger. The management plan transaction of gliclazide, and its detailed prescription format, is entered into the debit side of this ledger. The clinician makes the decision to start this patient on a medication called gliclazide for treatment of the diabetes mellitus on a dose of one daily.

Viewing this ledger account would clearly illustrate the management plan list, including therapeutics that are being received by the patient, on the debit side of this ledger. The transactions on the credit side are patient management goals.

examples
debit:
&ctx@rx@plan@+[gliclazide],tn[Diamicron],dose[80 mg],qty[1],freq[bd],pack[100],rpt[5]
credit:
&ctx@goal [diabetesMellitus],with[hemoGlobinGlycated],val[<7%]

8. Goal—rfe Ledger

This ledger takes management goal transactions on the debit side and reasons for encounter on the credit side. The debit transaction in this ledger is also matched by a credit transaction on the plan—goal ledger. Similarly the credit transaction in this ledger is matched by a debit transaction in rfe—history and examination ledger.

Viewing this ledger account would clearly illustrate the list of management goals on the debit side, associated with the reason for encounter on the credit side, providing a harmony of clinician's goals to match patient's needs. The planning goals create an expectation of questioning why the presence of these goals which are answered by the denouement given by the reasons for why the doctor was consulted in the first place—in this instance weight loss and tiredness. The stated goals are explained by the presentation in the first place. In a sense, then, this ledger account enables the medical record to go full circle. The scientific goal of keeping the glycated hemoglobin(HbA1c) within normal range is linked to the original symptomatic presentation. Problem-solving uses the concept of 'begin with the end in mind', and this ledger approach articulates on the goals of patient management. This aspect of 'patient treatment goals' is not well supported in prior art general medical record design.

An example of debit:
&ctx@goal [hemoGlobinGlycated],val[<70%]
An example of credit:
&ctx@seek@view[tiredness;weight@loss]

By way of an example of the above ledger operation, with respect to a clinical overview:

The patient presented with tiredness and weight loss. He gives a history of tiredness, thirst and weight loss for 2 months. On examination the doctor found chest rates but no wheezing. The differential diagnoses were chest infection and diabetes mellitus. He orders a glucose tolerance test. The result came back that the patient has diabetes mellitus. Treatment of gliclazide was given. A prescription of gliclazide was written. The treatment goal of maintaining glycated hemoglobin at less then 7 was noted.

>> Notary Function

One of the main current problems of electronic medical record is that of ensuring that medical records are not tampered with. The invention addresses the problem of proving the veracity and integrity of the electronic medical record, to a level that could be admissible in a court of law. Each medical medical transaction is represented as a character string, and each character string has a hash value that is expressed as a small integer 9 digits long.

Most modern software incorporates a hash function for converting a string to a number.

With a good hash function, the low-order bits of a character are deemed the most random ones, and the low order bits of the hash are of most interest, the ideal being to spread the low-order bits of several characters over the low-order bits of the result.

The notary functions of double entry medical recording system of the invention is implemented with the following steps.

Each transaction in the journal is held and sorted in chronological order.

Each transaction is subjected to a hashing function that returns the small integer number of 9 digits. As an example, utilising the hash function on Smalltalk VW3.0 on the following string:

'&ctx@ddx[diabetesMellitus;upperRespiratoryTractInfection]' returns the following number: 124194648, which functions just like a checksum.

The other function is the add function for linking this new hash number with the patient data checksum. The function called addNum below takes the first argument which represents the hash of the new transaction (a small integer expressed as a string), and adds it to a second number, being the patient data checksum (expressed as a string). These two numbers are added and expressed as a new string. The new checksum is the last 9 characters of this string.

addNum:num1 toNum: num2
|result numStr|
result:=''.
numStr:=(num1 asNumber)+(num2 asNumber).
result:=(numStr printString) last:9.
^result.

A checksum for each patient is held as a string representation in the field called the patient data checksum.

The old patient data checksum is inserted into the new transaction in its transactional checksum field.

The new computed checksum from the addNum operation above is copied to the patient data checksum.

The journal entries with their associated hash function numbers illustrates the process, the:

&ctx@hx[tiredness&ctx@ill(,6,mth);thirst*h&ctx@ill(, 1,mth);weight@loss&ctx@ill(, 10,k g,over,6,mth)] 115941696 intermediate checksum result: 115941696

&ctx@ddx[diabetesMellitus:upperRespiratoryTractInfection] 124194648 intermediate checksum result: 60729361

&ctx@ix@with[glucoseToleranceTest],for[diabetesMellitus] 110579745 intermediate checksum result: 58182189

&ctx@ix@with[glucoseToleranceTest],for[diabetesMellitus],find[glucoseToleranceTest&c tx@find,abnormal, high] 128378437 intermediate checksum result: 57666679

&ctx@dx[diabetesMellitus] 109523169
intermediate checksum result: 60809013
&ctx@rx@with[gliclazide],for[diabetesMellitus] 112672409
intermediate checksum result: 54099261
&ctx@rx[gliclazide&dose%,1,tab, mane&pack%80mg@tab@100&rpt%5&tn%Diamicron] 46599384
intermediate checksum result: 58194269
&ctx@rx@goal@for[diabetesMellitus],are [hemoGlobin@glycated%<7%] 128092729
intermediate checksum result: 56610353
Journal running hash checksum: 56610353

Likewise, each ledger has a checksum. The ledger checksum works in a similar way to the journal checksum. Any debit or credit to the ledger is simply added to the running total of the ledger checksum.

To ensure integrity of the system, after each posting on the journal, the system executes the debit entry before the credit entry.

Medical record checksum (MRC)=JournalChecksum+ ledger1Checksum+ledger1Checksum+ledger2Checksum+ ledger3Checksum+ledger4Checksum+ledger5Checksum+ ledger5Checksum+ledger6Checksum+ledger7Checksum+ ledger8Checksum Every time there a message is sent outside the domain of the medical record, the MRC is recorded. These messages could be on paper, such as prescription, referrals for tests, or could be electronic health messages or intentional notarising messages in the form of emails holding the MRC data. Once these Medical Record Checksums are sent outside the medical record environment it serves a notarising function as verification to the integrity of the system.

It should be noted that as each transaction is entered into a ledger, associated accrual balances are updated.

For example, a transaction such as &ctx@rx@with@+ [enalapril],for[hyper@tension] will cause the accrual context &ctx@rx@heap to be updated to be
&ctx@rx@heap[enalapril].

A further transaction down the track, such as &ctx@rx@with@+[gliclazide], for[diabetesMellitus], will cause the accrual balance
&ctx@rx@heap[enalapril;gliclazide].

Therefore each ledger contains the appropriate accrual balances. These running balances are of the accrual context type with the stigma of the suffix @heap. The accrued heap is not posted as a ledger entry. The heap cases are dynamic running balances and are not permanent entries.

A preferred embodiment of medical recording using a double entry accrual medical record will now be described by way of example.
&ctx@rx+[penicillin]
--> &ctx@rx@heap[penicillin]
&ctx@rx@+[warfarin]--> &ctx@rx@heap[penicillin; warfarin]
&ctx@rx@+[digoxin]--> &ctx@rx@heap[penicillin; warfarin;digoxin]
&ctx@-,digoxin
--> &ctx@on@heap[penicillin;warfarin]
Explanation of above example:
The first transaction means add penicillin to treatment heap.
The treatment heap is incremented with penicillin.
The second transaction means add warfarin to treatment heap.
The treatment heap is incremented to contain penicillin and warfarin.

The third transaction means add digoxin to treatment heap.
The treatment heap is incremented to contain penicillin and warfarin and digoxin.
The fourth transaction means remove digoxin from treatment heap.
The treatment heap is changed to contain penicillin and warfarin only.
Likewise the transactions for the accrual values associated with each ledger pertains to the allergy:
&ctx@drugReactions@allergy@+[penicillin]
--> &ctx@drugReactions@allergy@heap[penicillin]
&ctx@drugReactions@allergy@+[aspirin]
--> &ctx@drugReactions@allergy@heap[penicillin; aspirin]
The first transaction means add allergy to penicillin information to the drug allergy heap.
The drug allergy heap is updated to show allergy to aspirin.
The second transaction says add allergy to aspirin information to the drug allergy heap.
The drug allergy heap is updated to show allergy to aspirin and warfarin.
In another embodiment the following ledgers and transactions are identified:

---

'hxpx_eval' presentation/evaluation ledger
&ctx@hx[ weight@loss ; tiredness ; thirst; polyuria]
&ctx@?diabetesMellitus
&ctx@outx[weight@loss,better ; tiredness,worse]
&ctx@drugReactions@allergy@+[ penicillin]
&ctx@drugReactions@allergu@+[ warfain]
'eval_ixmx' evaluation/investigation/management ledger
&ctx@?diabetesMellitus
s@glucose
&ctx@dx@+[diabetesMellitus]
&ctx@rx@+[gliclazide]
&ctx@drugReactions@allergy@+[ penicillin]
&ctx@drugReactions@allergy@+[ warfain]
&ctx@warn@add,papSmear,overdue,by,20,day

---

The accrual balances in the ledger are:

---

&ctx@dx@heap[diabetesMellitus] 'diagnoses are heaped'
&ctx@udx@heap[chest@pain] 'pre-diagnoses are heaped'
( &etx@warn@heap[papSmear,overdue,by,20,day;]) " warnings are heaped"
'ix@find_eval' investigation/ evaluations ledger
s@glucose&ctx@find,abnormal,high,%10.8
&ctx@dx@+[diabetesMellitus]
&ctx@?diabetesMellitus
&ctx@warn@add,papSmear,overdue,by,20,day
'ix_ix@find' investigation/findings ledger
s@glucose
s@glucose&ctx@find,abnormal,high,%10.8
'mx@goal_hxpx' management goal/presentation
&ctx@rx@goal@for[diabetesMellitus],are[hemoGlobin@glycated%<7%]
&ctx@outx[weight@loss,better ; tiredness,worse]
'mx@plan_mx@goal'management/management goal ledger
&ctx@rx@add[gliclazide&dose%,1,tab,mane&pack%80mg@tab@ 100&rpt%5&tn%Diamicron]
&ctx@mx@plan@add[preventiveCare@carcinoma.cervix&ctx@by, papSmear,freq%lyi]
&ctx@rx@goal@for[diabetesMellitus],are[hemoGlobin@glycated%<7%]
(&ctx@mx@plan@heap[preventiveCare@carcinoma.cervix&ctx@by, papSmear,freq%lyi].)
'mx_mx@plan'management/management plan ledger
&ctx@rx@+[gliclazide]
&ctx@rx@+[gliclazide&dose%,1,tab,mane&pack%80mg@tab@ 100&rpt%5&tn%Diamicron]

The accrual balance for ledger shows:
&ctx@rx@heap[gliclazide&dose%,1,tab, mane&pack%80mg@tab@100&rpt%5&tn%/Dia micron]

Transactional Recording for Decision Support

This system and method of transactional recording comprises means for decision support including:

a) recording transactions in semiotic form two with components of evaluation, condition, outcome and means to achieve outcome for general patient population;

b) recording transactions in semiotic form two with antecedent components of symptoms, signs and tests, in order to achieve outcomes for diagnosis for general patient population;

c) seeking assistance with diagnosis and treatment for an individual patient using common criteria for queries on previous recording of such transactions and outcomes for other patients;

d) providing a patient database as a knowledge base, for decision support for subsequent patients with queries in semiotic form one.

The following gives examples that may be routinely entered for a series of patients:
&ctx@eval[emphysema],outx[,worse],with[infection]
&ctx@eval[pneumonia<streptoCoccus@pyogenes],outx [,cure],with[amox-ycillin]
&ctx@eval[rheumatoidArthritis],outx[,better],with [diclofenac@sodium]

The patient database can then be a knowledge base for decision support for subsequent patients with a query in semiotic form one:
? all rheua o :-)

This translates to: query all patients with rheumatoid arthritis with better outcomes, and the response from the system will list transaction such as:
&ctx@eval[rheumatoidArthritis],outx[,better],with [diclofenac@sodium]

Semiotic Form One—Detailed Description

Semiotic form one is a succinct language form, giving it more speed and less haze, and yet conveying the same meaning as verbose natural language. This approach addresses the intrinsic limitations in prior art methods involving pick lists, these pick lists usually comprising static pre-composed enumerated items, giving a tendency towards proliferation of coded items, difficulties in searching (due to the size of the pick lists), and a time consuming coding process (arising from an overabundance of mode changes).

Semiotic form two (eg. the DocleScript language) transcends both human and machine understanding, in order to represent patient and clinical data, and looks and acts like as high level computer language. For instance, to represent the clinical diagnosis of head injury in a motocar accident context the code is: &ctx@dx[injury.brain],ctx[,motorCarAccident], its abbreviated secondary key expression being: &ctx@dx [inju.brai],ctx[,mca].

Semiotic form one provides a complete solution to the doctor-machine interface problem, transcending even the power of DocleScript. The clinician requires to code for a complex scenario such as "Patient's diabetes mellitus is getting better with gliclazide". As explained, the invention offers an efficient natural language shorthand to bridge the man-machine communication gap. Semiotic form one (DocleTalk) is a natural and abbreviated way of communicating clinical intent.

To take an example, the following four expressions are equally effective to code or lead to the correct code for the scenario of a diabetic patient whose condition is improving with gliclazide.

1) diab :-) w glic
2) diabetes better with clazide
3) iabm :- w claz
4) mellitus :-) w licla Any four of the above, plus any number of minor variations will code for the following:
&ctx@eval[diabetesMellitus],outx[,better],with[gliclazide]

In plain English this translates to:
"In the subject matter of evaluation, the principal predicate value of 'diabetes mellitus', with predicate joiner for 'outcome' with subordinate predicate with value of 'better', with predicate joiner 'with' and a subordinate predicate containing value of 'gliclazide'."

In DocleTalk, the abbreviations and complete words used can be user-defined for customisation, and can include a complete range of emoticons—these can be used to code for patient clinical outcomes:
:-| patient in status quo
:-) patient is better
:-)) patient is much better
:-))) patient is cured
:-( patient is worse
:-(( patient is much worse
:-((( patient is moribund
o<-< patient deceased Semiotic form one is an ideal user interface language for clinicians, mapping to the next distinct semiotic form two (DocleScript), which provides precision and grace in medical storytelling in an age where there is a plethora of machines working amongst humans in the healthcare arena. This synergy of semiotic form one and semiotic form two greatly exceeds the utility found in the current numeric paradigms of medical coding.

The following provides additional technical description of semiotic form one (DocleTalk) and the transaction coder used to convert from semiotic form one to semiotic form two.

Semiotic form one usage is characterized by:

1) Simple sentence construct: genre followed by predicate and a series of joiner-predicate pairs.

2) Joiner is typically one character long or at worst—two or three or four character long.

3) Predicates are obtained by entering search tokens which are only a few characters long.

4) General sentence syntax modelled on semiotic form two to represent transaction.

5) Semiotic form one vocabulary of words predicated on the vocabulary of semiotic form two, which comprises primary, secondary and tertiary keys.

6) Use of acronyms and abbreviations, being secondary keys of semiotic form two, in order to attain effective matching with up to 100% confidence level;

7) Terse or verbose, misspelling-tolerant searching.

8) Plasticity of vocabulary allowing for shortcuts and aliasing to effect increased brevity.

9) Implied genre, pre-emptive guessing of transaction genre based on pattern analysis.

10) Single or multi-search tokens for probabilistic match.

11) Use of mostly one- or two- or three-character joiners. These joiners are contextual anchors to represent equivalent joiner attributes in semiotic form two. These joiners are interspersed among free text multi-token search patterns to effect genre specification and predicate list building.

12) Implied joiner, pre-emptive guessing of placement of joiner(s) based on interpretation of search patterns.

13) Mutation of joiners, based on interpretation of surrounding text.

14) Use of emoticons for patient outcomes with implied genre and implied joiner.

15) Use of a special characters, such as a semicolon to split up items within a predicate.

16) Use of numeric-based codes to represent clinical duration.

17) Probabilistic model of estimation of user intent, based on joiners and search strings to generate presence/clustering of certain medical terms, in order to infer probable user intent.

18) Use of the query context character "?" and the instructional context "!" at the beginning or at the end of the semiotic form one expression.

Semiotic form one is highly efficient in ensuring the system reliably reflects user intent based on a minimal number of keystrokes for inputs and queries, for both patient data and clinical knowledge bases.

The language definition is based on Extended Backus Naur Formalism (EBNF is discussed in 'Programming in Modula 2' by Niklaus Wirth, Springer-Verlag, 1982).

EBNF Syntax rules are defined as:
Syntax={rule}.
rule=identifier "=" expression ".".
expression=term {"|" term}.
term=factor {factor}.
factor=identifier|string|"("expression")"|"["expression"]
  "|"{" expression "}".
The right hand of each rule defines syntax based on previous rules and terminal symbols.
Parentheses such as ( ) group alternate terms.
The vertical bar separates alternate terms.
Square brackets [ ] denote optional expressions.
Braces { } denote expressions that may occur zero or more times.
EBNF Syntax for Semiotic Form One
docleOperators="!"|"<"|">"|"%"|"@"|"#"|"$"|"%"|"^"|"$"|"&"|"*"|",".
relationalOperator=">"|"<"|"="|"~"|">="|"#"
letter=capitalLetter
  |"a"|"b"|"c"|"d"|"e"|"f"|"g"|"h"|"i"|"j"|"k"|"l"|"m"|
  "n"|"o"|"p"|"q"|"r"|"s"|"t"|"u"|"v"|"w"|"x"|"y"|"z";
capitalLetter="A"|"B"|"C"|"D"|"E"|"F"|"G"|"H"|"I"|
  "J"|"K"|"L"|"M"|"N"|"O"|"P"|"Q"|"R"|"S"|"T"|
  "U"|"V"|"W"|"X"|"Y"|"Z".
digit="0"|"1"|"2"|"3"|"4"|"5"|"6"|"7"|"8"|"9".
number={digit}
numericModifier="."|"<"|">"|">="|"<="|"+"|"-"
numeric={[digit|numericModifier]}
character=|letter|digit|docleOperator
word{character}
searchPattern={word} {[""|"; "|", "|","|","] word}
searchPatternSeries={searchPattern}
genre="hx"|"px"|"hxpx"|"dx"|"rx"|"rfe"|"rv"|"ph"|
  "sh"|"fh"|"dx"|"ix"|"xi"|"mx"|"gx"|genreQueryInstruct|genreAliases
genreQueryInstruct="symptoms"|"signs"|"diff"|"ddx"|
  "dx"|"ix"|"xi"|"next"|"como"|"comorbidity"|"assoc"|
  "associations"|"differential
  diagnosis"|"diagnosis"|"treatment"|"presentation"|
  "find"|"findings"|"results"|"side
  effects"|"adr"|"adverse drug reactions"|"adverse"|
  "adverse effects"|"complications"|"comx"

scopeContext=|"stm"|"ltm"|"tr"|"this"|"all"|"patients"|
  "self"
genreAliases="p/"|"l/"|"u/"|"m/"|"s)"|"o)"|"a)"|"p)"
joiner=joiner1Character|joiner2Character|joiner3
  Character|joiner4Character|otherJoiner
joiner1Character="f"|"v"|"c"|"b"|"
  "|"o"|"u"|"w"|">"|"<"
joiner2Character="at"|"to"|"tn"|"by"|"->"|"<-"|"of"
joiner3Character="ctx"|"for"|"rpt"|"sans"|"val"|"who"|
  "why"|"how"|"but"
joiner4Character="bcos"|"dose"|"freq"|"find"|"from"|
  "give"|"mull"|"outx"|"pack"|"unit"|"with"|"when"|
  "what"
otherJoiner="consider"|"spec"|"specificity"|"sens"|
  "sensitivity"|"roi"|"returnOnInvestment"|"inci"| "incidence"|
durationUnit="3600"|"60"|"24"|"7"|"52"|"12"|"1"
timeInterval="si"|"mi"|"hi"|"di"|"wi"|"mthi"|"yi"
frequencyInterval=number timeInterval
duration=number "/" durationUnit
emoticonPatientOutcome=":-|"|":-)"|":-))"|":-)))"|":-
  (")|":-((")|":-((("|"o>->"
emoticonInvestigationControlOutcome="c:-|"|"c:-)
  "|"c:-))"|"c:-)))"|"c:-("|"c:-(("|"c:-(((
emoticon:=
  [emoticonPatientOutcome|emoticonInvestigationControlOutcome]
specialStrings=numeric|emoticon|frequencyInterval|
  duration|timeInterval
anchor=[genre|joiner]
codingExpression={[anchor] searchPatternSeries [specialStrings]}
subordinatePredicate=genre [relationalOperator word]
  |searchPatternSeries
queryExpression=["?"] [scopeContext] [genreQueryInstruct] ({[anchor] searchPatternSeries [specialStrings]
  }|subordinatePredicate) ["?"]
instructionalExpression=["!"] {[anchor] searchPattern
  Series [specialStrings]} ["!"] docleTalkExpression=codingExpression|queryExpression|instructionalExpression
Description of the Joiners
"f" translates to 'find' or 'for', mutable depending on context of surrounding words
"v" translates to val or value
"c" translates to "ctx" or context
"b" translates to "bcos" or because
"s" translates to "sans" or without
"o" translates to "outx" or outcome
"u" translates to unit
"w" translates to "with"
">" translates to "to" or sequela
"<" translates to "from" or antecedent
"to" means sequela
"tn" means trademark
"by" means by
"at" means by
"->" translates to "to"
"<-" translates to "from"
"ctx" means context
"who" means the person involved
"why" means for reason of
"how" means with
"for" means for as in duration or reason for
"rpt" means repeat
"sans" means without
"val" means value "bcos" means because
"dose" means the dose
"freq" means frequency
"find" means itself
"from" means antecedent
"give" means "to" or sequela
"mull" means to consider
"outx" means outcome
"pack" means medication pack
"unit" describes unit of measurement
"with" means along with.
"when" means datestamp
"what" means the object If, for example, the clinician wishes to enter the fact that the patient's gamma glutamyl transaminase result is abnormally high, he needs to type in semiotic form one:

xi ggt *h 447
Which returns:
&ctx@ix[s@gammaGlutamylTranspeptidase],find[,abnormal,high],val[447],unit[mmol/l]
xi ca *h 428
&ctx@ix[s@calc-ium],find[,abnormal,high],val[428],unit[mmol/l]
ca *h 428
&ctx@ix[s@calc-ium],find[,abnormal,high],val[428],unit[mmol/l]
ca 428
&ctx@ix[s@calc-ium],find[,abnormal,high],val[428],unit[mmol/l]

To give an example of where the joiners (acting as anchors) are needed:

bp 160/90

In this instance the lexical token of bp is totally descriptive of the term for blood pressure, while the term 160/90 qualifies as a value. The computer parser therefore automatically inserts a v (val or value anchor) into the expression, and prefixes the expression with px (the anchor for the physical examination genre):

px bp v 160/90

Some examples of query in semiotic form one with comments after hyphen:

? symptoms when diabm—symptoms of diabetes mellitus
symptoms diabm ?—symptoms of diabetes mellitus
? presentation of diabetesMellitus—symptoms and signs of diabetes mellitus
? treatment for diabm—treatment for diabetes mellitus
? ddx tiredness; weight@loss—differential diagnosis of chest pain and weight loss
? all with dx=diabm—search all patient data for cases of diagnosis of diabetes mellitus
? all with rx=warfarin—search all patient data for those on warfarin
? all with allergies=penicillin—search all patient data for those allergic to penicillin
? patients with diabm—search all patient data for diabetes mellitus
? all with diabm—search all patient data for diabetes mellitus
? ltm ddx chest@pain—search long term memory for differential diagnosis of chest pain
? presentation of diabetes—symptoms and signs of diabetes mellitus
? signs of rheuma—signs of rheumatoid arthritis
?signs aaa—signs of aortic artery aneurism
? ddx chest@pain—differential diagnosis of chest pain with short and long term memory
? dx chest@pain; hair@loss—differential diagnosis of presentation
? diff chest@pain—differential diagnosis of chest pain in default (tr=total recall=stm+ltm) memory
? diabm—symptoms, signs, abnormal tests, co-morbidities and treatment of diabetes
? diagnosis chest@pain—differential diagnosis of chest pain
? xi diabm—query abnormal test findings in diabetes mellitus
? ix diabm—query tests to do in diabetes mellitus
? ix chest@pain; weight@loss—query tests to follow up presentation
? next chest@pain; weight@loss—query tests to follow up presentation
? como rheua—co-morbidities of rheumatoidArthritis
? associations of diabetesMellitus—co-morbidities of diabetes mellitus
? when diabm—presentation + abnormal tests of diabetes mellitus
? find when diabetesMellitus—presentation + abnormal tests of diabetes mellitus
? findings when diabm—presentation + abnormal tests of diabetes mellitus
? results when diabm—abnormal tests with diabetes mellitus
? side effects gliclazide—query adverse reactions of the drug fliclazide
? adverse effects gliclazide—query adverse reactions of the drug fliclazide
? next skin@pigmentation*h—next symptom/sign/test to do
rx for diabetesMellitus ?—treatment for diabetes mellitus
? treatment for diabetesMellitus—same
? como carc.lung—associations of carcinoma lung
complications diabetes?—complications of diabetes mellitus
? comx diabm—complications of diabetes mellitus
? assoc diabm—co-morbidities of diabetes mellitus Some example constructs are now given of instruction in semiotic form one of the form ! when . . . consider . . . ["specificity" value] ["sensitivity" value] ["roi" value].

Examples:
! when tiredness consider diabetesMellitus—default values of 0.15 for specificity, sensitivity and returnOnInvestment
! when urine@output*h consider diabetesMellitus
! when jaundice; weight@loss; us.liver&ctx@find,abnormal; stools@pale consider neoplasm.liver
! when weight loss consider diabetes mellitus specificity 0.7 sensitivity 0.7 roi 0.8

A user-definable language as an alias mechanism can convert English type input to, say, French or German output. Coding allows for regional variation of abbreviations eg. fbc and fbe; cue and u&e The system thus involves on-demand 'de novo' synthesis of coded transactions, assembled from a natural language input. In marked contrast to conventional approaches, this does away with the reliance on a list of prescribed codes, and thus addresses the usual patient/computer interface problem. From the natural language input, the coding step to semiotic form two provides a system reflection of that input in the high level language of semiotic form two, provided in a user display in a pick list ranked by probability, for verification and acceptance by the user of the desired coding intent.

The following describes in further detail semiotic form two and its use with accrual transactions.

This language definition is also based on Extended Backus Naur Formalism (EBNF—see above).

The EBNF Syntax rules are defined as:

Syntax={rule}.
rule=identifier "=" expression ".".
expression=term {"|" term}.
term=factor {factor}.
factor=identifier|string|"("expression")"|"["expression"]"|"{" expression "}".

Unitary Health Language is a sequence of syntax rules.
The right hand of each rule defines syntax based on previous rules and terminal symbols.
Parentheses ( ) group alternate terms.
The vertical bar | separates alternate terms.
Square brackets [ ] denote optional expressions.
Braces { } denote expressions that may occur zero or more times.

```
docleWordSeparator:= "," | ";"
docleOperators =        "!" | "<" | ">" | "%" | "@" | "#" | "$" | "%" | "^" | "&" | "*" | ";"
letter = capitalLetter | "a" | "b" | "c" | "d" | "e" | "f" | "g" | "h" | "I" | "j" | "k" | "l" | "m"
  | "n" | "o" | "p" | "q" | "r" | "s" | "t" | "u" | "v" | "w" | "x" | "y" | "z".
capitalLetter = "A" | "B" | "C" | "D" | "E" | "F" | "G" | "H" | "I" | "J" | "K" | "L" | "M" | "N"
  | "O" | "P" | "Q" | "R" | "S" | "T" | "U" | "V" | "W" | "X" | "Y" | "Z".
digit = "0" | "1" | "2" | "3" | "4" | "5" | "6" | "7" | "8" | "9".
character = | letter | digit | docleOperator
docleWord = { character }
attributeJoiner = "about" | "above" | "across" | "after" | "against" | "aheadOf" | "along" |
  "although" | "among" | "and" | "around" | "as" | "ask" | "at" | "author" | "because" |
  "behind" | "because of" | "below" | "before" | "beneath" | "beside" | "between" | "but" |
  "by" | "coda" | "consider" | "ctx" | "date" | "dateEvent" | "dose" | "down" | "during" |
  "except" | "fact" | "find" | "for" | "frequency" | "from" | "go" | "how" | "if" | "in" |
  "inFrontOf" | "insteadOf" | "into" | "ix" | "like" | "more" | "near" | "nextTo" | "not" |
  "note" | "of" | "on" | "onto" | "original" | "outcome" | "over" | "pack" | "quantity" | "repeat"
  | "sans" | "start" | "stop" | "since" | "that" | "though" | "through" | "throughout" |
  "tradename" | "to" | "toward" | "under" | "unit" | "unless" | "until" | "up" | "value" |
  "when" | "whether" | "while" | "who" | "why" | "with" | "within" | "without" | "yet"
subjectGenre = "genre@hxpx" | "genre@phx" | "genre@fh" | "genre@sh" | "genre@rfe" |
  "genre@eval" | "genre@ix@find" | "genre@ix" | "genre@goal" | "genre@plan" |
  "genre@mx" | "genre@admn"
subjectSpecies = "&ctx@admn" | "&ctxc@rx" | "&ctx@ppoc" | "&ctx@rx@plan"
  "&ctx@ppoc@plan" | "&ctx@mx@goal" | "&ctx@ix" | "&ctx@dx" | "&ctx@?"
  | "&ctx@udx" | "&ctx@?@ai" | "&ctx@drug@allg@+" | "&ctx@drug@adr@+" |
  "&ctx@eval" | "&ctx@warn" | "&ctx@warn@ai" | "&ctx@seek@view" |
  "&ctx@seek@re@view" | "&ctx@hx" | "&ctx@px" | "&ctx@hxpx" | "genre@phx"
  | "&ctx@fh" | "genre@sh"
predicateList = "" | {docleWord} {[docleWordSeparator] docleWord}
predicate = attributeJoiner "[" predicateList "]"
sentence = subjectSpecies "[" predicateList "]" {predicate}
exoSkeletalCast = subjectSpecies "[" "]" { attributeJoiner"["  "]" }
exoskeletalCast constraints in Smalltalk language:
getGenreSpecies: aGenre
(aGenre ='genre@hxpx' ) ifTrue:[ ^#( '&ctx@hx[ ]' '&ctx@hx[ ],ctx[ ]' '&ctx@hx[ ],ctx[
],for[ ]' '&ctx@hx[ ],for[ ]' '&ctx@hx[ ],sans[ ]' '&ctx@px[ ]' '&ctx@px[ ],val[ ]'
'&ctx@hxpx[ ],for[ ]' '&ctx@hxpx[ ],find[ ],for[ ]' '&ctx@px[ ],find[ ],val[ ]' '&ctx@px[
],sans[ ]' '&ctx@hxpx[ ]' '&ctx@hxpx[ ],ctx[ ]' '&ctx@hxpx[ ],sans[ ]' ) ].
(aGenre ='genre@phx' ) ifTrue:[ ^#( '&ctx@phx[ ]' '&ctx@phx[ ],sans[ ]' ) ].
(aGenre ='genre@fh' ) ifTrue:[ ^#( '&ctx@fh[ ]' '&ctx@fh[ ],sans[ ]' ) ].
(aGenre ='genre@sh' ) ifTrue:[ ^#( '&ctx@sh[ ]' '&ctx@sh[ ],sans[ ]' ) ].
(aGenre ='genre@rfe' ) ifTrue:[ ^#( '&ctx@seek@view[ ]' '&ctx@seek@view[ ],ctx[ ]'
'&ctx@seek@view[ ],for[ ]' '&ctx@seek@view[ ],find[ ]' '&ctx@seek@re@view[ ]'
'&ctx@seek@re@view[ ],for[ ]' '&ctx@seek@re@view[ ],find[ ]' '&ctx@seek@re@view[
],ctx[ ]') ].
(aGenre ='genre@eval' ) ifTrue:[ ^#( '&ctx@dx[ ]' '&ctx@dx[ ],with[ ]' '&ctx@dx[
],to[ ]' '&ctx@dx[ ],from[ ]' '&ctx@dx[ ],ctx[ ]' '&ctx@?[ ]'      '&ctx@udx[ ]'
'&ctx@?@ai[ ]' '&ctx@drug@allg@+[ ],to[ ]' '&ctx@drug@adr@+[ ],to[ ]'
'&ctx@eval[ ]' '&ctx@eval[ ],outx[ ]'
'&ctx@warn[ ]'
  '&ctx@warn@ai[ ]' ) ].
(aGenre ='genre@ix@find' ) ifTrue:[ ^#( '&ctx@ix[ ],find[ ],val[ ]' '&ctx@ix[ ],find[ ]' ) ].
(aGenre ='genre@ix' ) ifTrue:[ ^#( '&ctx@ix[ ],for[ ]' ) ].
(aGenre ='genre@goal' ) ifTrue:[ ^#( '&ctx@mx@goal[ ]' '&ctx@mx@goal[ ],val[ ]'
'&ctx@mx@goal[ ],val[ ],for[ ]' '&ctx@mx@goal[ ],find[ ]' '&ctx@mx@goal[ ],find[ ],for[ ]')].
(aGenre ='genre@plan' ) ifTrue:[ ^#( '&ctx@rx@plan[ ]' '&ctx@ppoc@plan[ ]'
'&ctx@ppoc@plan[ ],val[ ]'
                                                                '&ctx@rx@plan[ ],tn[
],form[ ],dose[ ],qty[ ],freq[ ],pack[ ],rpt[ ],more[ ]')
                            ].
"the genre@mx"
(aGenre ='genre@mx' ) ifTrue:[ ^#( '&ctx@rx[ ]' '&ctx@rx[ ],for[ ]' '&ctx(@ppoc[ ]'
'&ctx@ppoc[ ],for[ ]'     ) ].
"the genre@adnm "
(aGenre ='genre@admn' ) ifTrue:[ ^#('&ctx@admn[ ]' )
```

Constraints of the predicate list are implemented at the semiotic form two transaction coder. A constraint may also be implemented at the semiotic form three level using standard SQL table constraints.

An example is that the predicate list is of drugs only when the subjectSpecies of &ctx@drug@allg@+ |&ctx@drug@adr@+|&ctx@rx are therapeutics specific.

Likewise a subjectSpecies of &ctx@ix will constrain the predicate list to terms of types diagnostic imaging or diagnostic non-imaging words only.

Akin to the balances of accounting ledgers, the running balances of the double entry recording of transactions has its balances held in accrual tables:

Using the example of:
dx diabm +

This leads to the transaction of semiotic form two being built:
&ctx@dx@+[diabetesMellitus],note[ ],auth[yko],coda[ ]

The above transaction has a + stigma on the contextual organizer and will lead to accrual actions on the accrual table:
&ctx@dx@heap[diabetesMellitus],note[ ],auth[yko], coda[ ]
dx ra+

This leads to the transaction of the semiotic form two being built:
&ctx@dx@+[rheumatiodArthritis],note[ ],auth[yko], coda[ ]

The above transaction has a + stigma on the contextual organizer and will lead to accrual actions on the accrual table:
&ctx@dx@heap[diabetesMellitus;rheumatoidArthritis], note[ ],auth[yko],coda[ ]

It is possible to recalculate the accrual table entries for each patient.

The accrual table holds summary information regarding the patient for the fundamental areas of active problem list, list of treatments, list of allergies, and list of undiagnosed problems.

Under appropriate circumstances, one transaction can trigger one or more accessory transactions. For example in coding for a test result:
&ctx@ix[s@glucose],find[diabetesMellitus],val[10.5]

it is appropriate that the system generates and prompts for the following accessory implied transaction to be accepted:
&ctx@dx@+[diabetesMellitus]

Coded transaction of semiotic form two can be disaggregated into two or more transactions. For example:
&ctx@dx@+[diabetesMellitus;chronicRenalFailure] . . . can be disaggregated into:
&ctx@dx@+[diabetesMellitus]
&ctx@dx@+[diabetesMellitus]

Similarly, in semiotic form two, two or more transactions can be aggregated into a single transaction. For example:

| &ctx@seek@view[dyspnea] &ctx@seek@view[chest@pain] &ctx@seek@view[dyspnea;chest@pain] | . . . can be aggregated into: |
|---|---|

Certain coded transactions (of semiotic form two) have the property of tautomerism, in that a new transaction with the same meaning can be constructed from an old one by the reshuffling of the segments and using new joiner attributes. For example:

&ctx@dx[cata-ract;anem-ia;blindness],from[chronicRenalFailure] . . . can be computed to the isomeric transaction of:
&ctx@dx[chronicRenalFailure],to[cata-ract;anem-ia; blindness]

All coded transactions (of semiotic form two) can be paraphrased into other medical codes using namespace nomenclature and thus effectively confer transactional capabilities to older numeric coding paradigms. For example:
&ctx@dx[chronicRenalFailure] . . . can be in ICD9 as:
&ctx@dx[icd9@585@=@crf]
while:
&ctx@dx[cata-ract;anem-ia],from[chronicRenalFailure]
&ctx@dx[icd9@366.19@=@cataract; icd9@285.9@=anem;blindness],from [icd9@585@=@crf]

For coded transactions in semiotic form two, a 'coda' attribute contains the version number of the semiotic definition. For example:
&ctx@dx[cata-ract;anem-ia],from[chronicRenalFailure], coda[v2]

The coda signifies a semiotic version 2, and this designation may assist with the translation of older semiotic constructs.

Semiotic form two transactions can be used to describe the individual component codes eg. the mrsa code is: infection<staphyloCoccus@aureus@resistant@meth-icillin, which has the following semiotic form two descriptions in its properties:
infection<staphyloCoccus@aureus&ctx [resistance@drug],to[methicillin]

Namespace—Tertiary Keys

In this invention, namespaces are used to unify other medical codes for conversion to and from the various semiotic forms two, three and four. This helps create an effective and seamless medical coding space by mass scale importation of foreign termsets into resident coding space using this system of tertiary keys composed from concatenation of namespace-relational operator-in situ secondary key.

The system of namespaces allows the incorporation of other term sets, such as ICPC terms, ICD10AM, Snomed terms and SNOMED-CT concepts into a unified Docle coding space. Other term sets are mapped into the unified coding space as namespace-tertiary keys.

The reporting of the relationships between Docle terms and other terms/concepts from other term sets utilises map relationship definitions covering the relationships of: 'equal to', 'broader than', 'much broader than', 'narrower than', 'much narrower than', 'not equal to', and 'partial fit'.

This approach involves the creation of separate 'namespaces' for the various coding systems. A designated namespace key and associated operators are used for matches, being partial, much narrower than, narrower than, broader than, much broader than and equal to those under the unified Docle Namespace.

Codes from other termsets are therefore generated by adding a prefix consisting of the namespace and the mathematical measure of fit, along with associated @ operators, to the code itself as the suffix, in order to generate a namespace-tertiary key. These keys are recognisable by a parser because of their unique namespace designation. This system allows the seamlessly blending of other coding system codes into the Docle Linnean medical hierarchy and, as an intrinsic characteristic of the namespace-tertiary key system, is auto-reflective as to the degree of match. The use of relationship operators allows the mapping of a fine grain system—such as Docle, with over 30,000 terms—to a smaller coarse grain system such as ICPC with several thousand terms. Adoption of coding namespaces thus affords the unification of all medical terminology into a unified medical namespace of this invention.

Each created and embedded namespace constructs preferably comprises a key (a readable expression) having components (a) a designated namespace, (b) a medical code in an otherwise incompatible format, (c) a relational operator to depict the quality of match, and (d) a self-descriptive term to obviate the need for a lookup table.

The following describes the operation of this system.
Namespaces are declared as below.
A notational system is used for keys
The namespace for the ICD9 codes has the prefix icd9@.
The namespace for the ICD codes has the prefix icd10@.
The namespace for the ICPC codes has the prefix icpc@.
The namespace for the READ codes has the prefix read@.
The namespace for ean codes has the prefix ean@.
The namespace for the SNOMED CT codes has the prefix snct@.

Terms and other terms/concepts from other termsets will be defined by using map relationship definitions of equal to, broader than, much broader than, narrower than, much narrower than, not equal to, and partial fit.

The operators are:

| | |
|---|---|
| identical | == |
| equal to | = |
| broader than | > |
| much broader than | >> |
| narrower than | < |
| much narrower than | << |
| not equal to | >< |
| partial fit | <> |

For example, coding of the item 'arthritis':
primary key: arthritis
secondary key: arth
tertiary keys: jointInflammation
namespace tertiary keys: icd9@716.9@=@arth
   icd10@M13.99@=@arth
   icd9@714.0@<<@arth The last statement signifies that rheumatoid arthritis is much narrower than arthritis.
Coding of the item rheumatoid arthritis:
primary key: rheumatoidArthritis
secondary key: rheua
tertiary keys: ra
namespace tertiary keys: icd9@714.0@=rheua
   icd10@M06.99@=@rheua
   icd9@714@< >@rheua
   icd9@714.1@< >@rheua
   icd9@716.9@>@rheua
   icd9@715.9><@rheua
Where:
icd9 code 714.0 is for rheumatoid arthritis.
icd9 code 714 is for juvenile rheumatoid arthritis.
icd9 code 714.1 is felty syndrome-hypersplenism associated with rheumatoid arthritis.
icd9 code 716.9 is arthritis.
icd10 code M13.99 is for arthritis
icd10 code M06.99 is for rheumatoid arthritis
icd9 code 715.9 is osteoarthritis This namespace-tertiary keys system therefore allows the seamless mixing of codes based on one or a plurality of medical coding schemes in a single transaction into single unified semiotic form two coded transaction utilizing namespace-tertiary keys.

The example below is in semiotic form two:
&ctx@rx[diclofenac],for[rheumatoidArthritis].
Mixing ean codes with ICD 9 codes.
&ctx@rx[ean@123456789],for
   [icd9@714.0@=@rheua].

The namespace-tertiary keys system thus affords unification of all medical coding systems and extends transactional capabilities and a language framework for older medical coding systems that lack a linguistic construct.

Unique Patient Identifiers

The method and system of the invention addresses the problem of a lack of unique patient identifiers. A dependence on national medical care numbers (eg Medicare numbers or NHS numbers) is unreliable, as such numbers are very difficult to readily verify, consisting only of code numbers/characters. Increasing use of Medicare numbers has lead to greater entropy in the healthcare system. Studies by the inventor have concluded that a solution to the problem of patient identifiers should involve the participation of general practitioners, in conjunction with the appropriate administrative bodies, as naming conflicts need to be resolved by GPs, and GPs have to maintain and attest to the integrity and veracity of the system. In the first instance, a patient can choose to opt out of the system, in which case the uniqueness of these patient keys is resolved through the levels of the appropriate administrative bodies.

Patient (species) naming conflicts are resolved by using the typical biblical naming series found in Matthew 1:2 where is found the name series of "Abraham was the father of Isaac; Isaac was the father of Jacob; Jacob was the father of Judah; Judah was the father of Perez . . . (Tamar was his mother) . . . "

Naming conflicts, in the event that there were many of the name Perez in the particular community at that particular historical period, this can be resolved by naming this particular Perez as:

perez_s_judah_tamar_jacob_isaac_abraham where s means son of.

The framework of the linnean Docle paradigm of unique patient identifier views each patient as a unique individual requiring a species name.

In the Docle classification framework there are primary, secondary and tertiary keys: e.g. diabetesMellitus is a primary key, while the secondary key is diabm and the tertiary keys which are really aliases, such as "sugar_diabetes", or simply "diabetes". In the proposed linnean ID system, the primary key for a given individual is yet to be developed at his time, and a national Patient ID is implemented, the linnean ID will be its secondary key.

The linnean ID secondary key incorporates the elements of first name, a computed number derived from the date of birth, the sex, the surname of father, and the first names of father and mother. The coda of this linnean ID key contains the divisional namespace after the apropos sign. Patients are registered at the divisional level, the division being the local GP administrative grouping (eg, in Australia, a division of the ADGP).

Given a hypothetical individual example, Robert was born on 17 Mar. 1988 with father David and mother Alyce and registered by his family doctor on 6 Jun. 2002.

He will be classified with the species name of:
robert31852s@david@alyce.020606.vic.au the derivation of key being from:
[first name at birth] [date of birth as expressed as number of days from 1 jan 1901] [s|d]
"@"[firstname of father] "@" [first name of mother] "."
dateRegistration [state]
"."[country]
dateRegistration=yymmdd format This system is suitable for women who wish to change their surnames on marrying.

The s|d option signifies 's' for son of, and 'd' for daughter of.

A family GP is the 'registrar' of a particular kay, responsible for the integrity and custodianship of the Linnean ID system. The GP duties include sighting original documents, generating the Linnean ID, and educating the patient with regard to the Linnean ID. Verification of patient identity is a responsibility GPs are traditionally used to. If appropriate, use of the identifiers can involve a small reward for each patient registration of the Linnean ID key, to both doctor and patient, due to the savings generated from increased efficiency of process arising out of this use.

The name of the division indicates the origin of a particular Linnean ID key, as well as the fact that it is a linnean ID. Further, the name of the division indicates the location of the registrar the ID key.

In the extremely rare event that there is another individual with the same administrative data as Robert in that same division, then the key is simply resolved on the following registration day:
robert31852s@david@alyce.020607.vic.au The division collects information in a data table (a relational database) comprising only three fields: the Linnean ID key, the attribute of the registrar (the provider number), and the national medical care number (eg Medicare number) of the patient (if available). Before a new Linnean ID is created, a check is made on the national database for duplication of ID. For example if another GP in the Dandenong division attempts to enrol Robert, the national database check will indicate that Robert is already enrolled in the Knox division via information regarding Medicare number and date of birth.

The system is designed to maintain full integrity. The database at the general practitioner divisional level can be uploaded to a regional divisional office (eg the state divisional office). Duplicates are detected by looking for records with the same date of birth-computed number, and the same medical number, as well as by other checks. Intentional and unintentional risks of system corruption can be detected by a doctor unable to match pathology results and hospital discharge notes. In this way, patients can be taught to value the advantages of a safe and accurate ID that has as its sole aim improved health outcomes. The integrity of the system is maintained by constant use, and dubious Medicare numbers will be exposed by such use.

Currency and integrity of each key must be certified every two years by the GP or approved health care provider.

The system deals with Linnean ID key deprecation in this way. The division at national level constructs a table of deprecated keys, being keys that will never be used again. Each deprecated key will point to the current Linnean ID. Doctors and patients involved in any key deprecation are informed by the division. The system is thus designed to withstand key deprecation.

The following gives further information on the Linnean classification of patients:
kingdom: objectMedica
phylum: tamtap
class:
order:
family:
genus: robert^ 33679^ s^ d^ father@david^ mother@alyce^ 020606.vic.au^
species: robert31852s@david@alyce.020606.vic.au
Comment: the Linnean Id belongs to the polygenera of: robert^ 33679^ s^ d^ father@david^ mother@alyce^ 020606.vic.au^

The Linnean ID system will pick up most if not all incongruencies in entries. The enhanced reliability and efficiency of the system will tend to encourage buy-in from all stakeholders in the medical community. It is commonly understood that 20% of our patients make more than 80% of healthcare demands. If the system can concentrate on the healthcare needs of this 20 percent, and demonstrate the fairness and integrity of the system, the rest of the population will buy in.

Further Examples:
david_33679_s_oon_yeong_juliet@knox@2002
david33679s@yeong@juliet.02.vic.au
reads as—David, born 33679 days after 1 Jan. 1901, son of Yeong, of Juliet, located in year 02, located in Victoria, located in Australia
nicole33094s@yeong@juliet.02.vic.au
reads as—Nicole, born 33679 days after 1 Jan. 1901, daughter of Yeong, of Juliet, located in year 02, located in Victoria, located in Australia Technical Solution to the Problem of Remoting In addition to the above, the method and system of the invention addresses the problem of remoting. The data object used to encapsulate the medical data (the transactions) is a DataSet object. This DataSet object is a cached fragment of a database that can be distributed across application domains and processes for data manipulation.

In essence, remoting a medical record involves the deconstruction of medical recording into transactions written up in DocleScript, a unitary health language, and wrapping this in SGML, preferably in XML schema and XML messages.

Embodiments of the XML schema diagram are given below.

```
<?xml version="1.0" standalone="yes"?>
<xsd:schema id="NewDataSet" targetNamespace="" xmlns=""
  xmlns:xsd="http://www.w3.org/2001/XMLSchema" xmlns:
  msdata="urn:schemas-microsoft-com:xml-msdata">
  <xsd:element name="NewDataSet" msdata:
    IsDataSet="true" msdata:Locale="en-AU">
    <xsd:complexType>
      <xsd:choice maxOccurs="unbounded">
        <xsd:element name="Transactions">
          <xsd:complexType>
            <xsd:sequence>
              <xsd:element name="PatientID" type="xsd:
                string" minOccurs="0" />
              <xsd:element name="DocleScript" type="xsd:
                string" minOccurs="0" />
            </xsd:sequence>
          </xsd:complexType>
        </xsd:element>
      </xsd:choice>
    </xsd:complexType>
  </xsd:element>
</xsd:schema>
```

Embodiment of the "reason for encounter" transaction wrapped in XML: The transaction in XML simplified to show only the transactional contents"

```
<?xml version="1.0" standalone—"yes"?>
<NewDataSet>
<Transactions>
    <PatientID>213424242</PatientID>
    <DocleScript>&ctx@seek@view[back@pain;
    chest@pain],note[yko]</DocleScript?
</Transactions>
</NewDataSet>
```

Embodiment of the "symptoms" transaction wrapped in XML:

The transaction in XML simplified to show only the transactional contents"

```
<?xml version="1.0" standalone="yes"?>
<NewDataSet>
<Transactions>
    <PatientID>213424242</PatientID>
    <DocleScript> &ctx@hx[weight@loss; tiredness thirst
    polyuria],sans[hear-t@palpitations],note[yko]</DocleScript>
</Transactions>
</NewDataSet>
```

Embodiment of the "signs or physical examination findings" transaction wrapped in XML: The transaction in XML simplified to show only the transactional contents"

```
<?xml version="1.0" standalone="yes"?>
<NewDataSet>
<Transactions>
    <PatientID>213424242</PatientID>
    <DocleScript> &ctx@px[chest@rales;
    wheezing],sans[leg@pain@touch],note[yko]</DocleScript>
</Transactions>
</NewDataSet>
```

Embodiment of the "signs or physical examination findings" transaction wrapped in XML: The transaction in XML simplified to show only the transactional contents

```
<?xml version="1.0" standalone="yes"?>
<NewDataSet>
<Transactions>
    <PatientID>213424242</PatientID>
    <DocleScript> &ctx@px[chest@rales;
    wheezing],sans[leg@pain@touch],note[yko]<DocleScript>
</Transactions>
</NewDataSet>
```

This is a simplified schema, as clearly the date of encounter has to be recorded as an element of the XML encoded transaction, eg:

<DateTime> 12 Apr 2002</DateTime> or alternatively a scheme can be devised to incorporate the date information within DocleScript itself, eg:

12 apr 2002 &ctx@seek@view[back@pain;chest@pain], note[yko]

The invention claimed is:

1. A computer-based method of recording medical transactions through de novo composition and construction of medical transaction codes; including the steps of:
   inputting medical transactions in a semiotic form one, the semiotic form one input being a free form-type, abbreviation-oriented natural language textual input,
   parsing said semiotic form one input and converting it into coded medical transactions in a semiotic form two output, the transaction codes composed and constructed de novo, the semiotic form two output embodying high level machine-parseable computer language statements comprehensible to a high certainty level by human users,
   causing a user display to display system reflection in the form of coded medical transactions in said semiotic form two and system-rated confidence levels representing the match between a code and correspondence with perceived user intent,
   receiving user selection input for verifying a selected coded medical transaction,
   converting a semiotic form two input into a semiotic form three transaction by mapping the selected coded transaction into data row in a relational database to render the transaction data amenable to structured query language processing,
   wherein each coded medical transaction in semiotic form two is classified into a genre selected from the group: (a) reason for encounter: genre@fie; (b) symptom/sign: genre@hxpx; (c) past history: genre@hxpx; (d) social history: genre@hxpx; (e) family history: genre@hxpx; (f) diagnosis or evaluation: genre@eval: (g) test: genre@ix; (h) test result: genre@ix@find; (i) drug or procedural treatment: genre@mx; (j) management plan—prescription specification: genre@plan; and (k) management goal: genre@goal, and
   wherein each coded medical transaction belongs to a species, each species being a classification under a genre.

2. The method of claim 1, wherein coded medical transactions in semiotic form two include segments comprising one or more thematic codes demarcated by punctuation characters, segments being joined together using attribute joiners to enable representation of all possible clinical scenarios.

3. The method of claim 1, including the step of enabling a user viewing coded and the non-coded segments of transactions in semiotic form two to augment uncoded segments with free text comments into uncoded segments.

4. The method of claim 1, including disaggregating a transaction in semiotic form two into two or more transactions.

5. The method of claim 1, including aggregating two or more transactions in semiotic form two into a single transaction.

6. The method of claim 1, wherein a natural language textual input forms a subcomponent of a medical transaction once converted into semiotic form two.

7. The method of claim 1, wherein semiotic form three transactions are stored in a fully parsed state in a relational database table.

8. The method of claim 1 including the step of a further transaction conversion to convert a semiotic form two input or a semiotic form three input into a semiotic form four transaction by marking up with a markup scripting language, in order to facilitate electronic sharing of medical data.

9. A computer-based method of recording medical transactions through de novo composition and construction of medical transaction codes: including the steps of:
   inputting medical transactions in a semiotic form one, the semiotic form one input being a free form-type, abbreviation-oriented natural language textual input,
   parsing said semiotic form one input and converting it into coded medical transactions in a semiotic form two output, the transaction codes composed and constructed de novo, the semiotic form two output embodying high level machine-parseable computer language statements comprehensible to a high certainty level by human users,
   causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing, and including extracting a transaction in semiotic form two as an exoskeletal cast independent of the data content held within.

10. The method of claim 9, wherein the exoskeletal cast constrains the codes permitted within a segment to ensure semantic integrity.

11. A computer-based method of recording medical transactions through de novo composition and construction of medical transaction codes; including the steps of:

inputting medical transactions in a semiotic form one, the semiotic form one input being a free form-type, abbreviation-oriented natural language textual input, parsing said semiotic form one input and converting it into coded medical transactions in a semiotic form two output, the transaction codes composed and constructed de novo, the semiotic form two output embodying high level machine-parseable computer language statements comprehensible to a high certainty level by human users, causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing, wherein coded medical transactions in semiotic form two include a coda attribute containing the version number of a semiotic definition.

12. The method of claim 11, wherein the coda attribute additionally contains trailing information regarding user log data and/or system access data and/or user-specified comment data and/or user visibility data.

13. A computer-based method of recording medical transactions through de novo composition and construction of medical transaction codes; including the steps of:

inputting medical transactions in a semiotic form one, the semiotic form one input being a free form-type, abbreviation-oriented natural language textual input, parsing said semiotic form one input and converting it into coded medical transactions in a semiotic form two output, the transaction codes composed and constructed de novo, the semiotic form two output embodying high level machine-parseable computer language statements comprehensible to a high certainty level by human users, causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing, wherein each coded medical transaction in semiotic form two includes a genre specifications which contains an accrual trigger.

14. The method of claim 13, wherein use of a transaction with an accrual trigger operates on a heap transaction of an appropriate genre specification to generate a new accrual heap transaction in an accrual table.

15. A computer-based method of recording medical transactions through de novo composition and construction of medical transaction codes; including the steps of:

inputting medical transactions in a semiotic form one, the semiotic form one input being a free form-type, abbreviation-oriented natural language textual input, parsing said semiotic form one input and converting it into coded medical transactions in a semiotic form two output, the transaction codes composed and constructed de novo, the semiotic form two output embodying high level machine-parseable computer language statements comprehensible to a high certainty level by human users, causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing, wherein coded medical transactions in semiotic form two include embedded namespace constructs for import mapping of medical codes in otherwise incompatible formats.

16. The method of claim 15, wherein each said embedded namespace constructs comprises a key being a readable expression having components (a) a designated namespace, (b) a medical code in an otherwise incompatible format, (c) a relational operator to depict the quality of match, and (d) a self-descriptive term to obviate the need for a lookup table.

17. The method of claim 15, wherein the coded medical transactions are adapted to be format-agnostic.

18. A computer-based method of recording medical transactions through de novo composition and construction of medical transaction codes; including the steps of:

inputting medical transactions in a semiotic form one, the semiotic form one input being a free form-type, abbreviation-oriented natural language textual input, parsing said semiotic form one input and converting it into coded medical transactions in a semiotic form two output, the transaction codes composed and constructed de novo, the semiotic form two output embodying high level machine-parseable computer language statements comprehensible to a high certainty level by human users, causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing, wherein coded medical transactions in semiotic form two are configured to enable export mapping into medical codes in otherwise incompatible formats, including older numeric type codes using namespace nomenclature.

19. A computer-based method of recording medical transactions through de novo composition and construction of medical transaction codes; including the steps of:
   inputting medical transactions in a semiotic form one, the semiotic form one input being a free form-type, abbreviation-oriented natural language textual input,
   parsing said semiotic form one input and converting it into coded medical transactions in a semiotic form two output, the transaction codes composed and constructed de novo, the semiotic form two output embodying high level machine-parseable computer language statements comprehensible to a high certainty level by human users,
   causing a user display to display system reflection in the form of coded medical transactions in said semiotic form two and system-rated confidence levels representing the match between a code and correspondence with perceived user intent,
   receiving user selection input for verifying a selected coded medical transaction,
   converting a semiotic form two input into a semiotic form three transaction by mapping the selected coded transaction into data row in a relational database to render the transaction data amenable to structured query language processing, wherein the step of converting into said semiotic form three transaction involves deconstruction of said medical transaction in semiotic form two in accordance with genre, transaction cast and joiner attributes, to be refactored into the data row in a table of transactions with genre and joiner attributes.

20. A system for recording medical transactions, the system comprising distinct and multi-linguistic representation layers, allowing the de novo composition and construction of medical transaction codes; including:
   a user interface including means for inputting medical transactions in a semiotic form one, the semiotic form one input being a free form-type, abbreviation-oriented natural language textual input,
   a transaction parser-coder configured to parse said semiotic form one input and to convert it into coded medical transactions in a semiotic form two output, the transaction codes composed and constructed de novo, the semiotic form two output embodying high level machine-parseable computer language statements comprehensible to a high certainty level by human users,
   means for evoking a display of system reflection in the form of coded medical transactions in said semiotic form two and system-rated confidence levels representing the match between a code and correspondence with perceived user intent,
   means for receiving user selection input for verifying a selected coded medical transaction,
   a transaction mapper configured to convert a semiotic form two input into a semiotic form three transaction by mapping the selected coded transaction into data row in a relational database to render the transaction data amenable to structured query language processing, and
   a text editor having an interface for enabling a user to compose semiotic form one input using a minimal number of keystrokes to compose medical transactions during a clinical consultation to document medical history, findings, evaluations, management and planning, each key component of the transaction being abbreviated down to an abbreviation of maximum four characters.

21. The system of claim 20, wherein the semiotic form one and the transaction parser-coder are designed to be misspelling intolerant and compatible with both brief and verbose free-form input.

22. The system of claim 20, the semiotic form three including the encapsulation of information pertaining to the genre and decomposition of the transaction, the system including means for analysis and viewing of transactions, and means for realising accrual functions in transaction debit and credit ledgers, to allow the synchronisation of distributed medical records.

23. The system of claim 22 for use in combination with a distributed network, including means for double entry accounting of transactions for medical record synchronization and accrual operations for selected transactions.

24. The system of claim 20 including a markup converter configured to convert a semiotic form two input or a semiotic form three input into a semiotic form four transaction by marking up with a markup language in order to facilitate electronic sharing of medical data.

25. The system of claim 20 configured to allow input at any of the linguistic representation layers and to enable lay and professional users to create, interrogate, integrate, process, view, update and use a part or whole of the medical transaction data.

26. The system of claim 20, the text editor interface including a single text pane for user entry of all types of medical transactions relating to patient health care.

27. The system of claim 26, said single text pane used to enter an entire narration of patient encounter notes, the system including means for and comprising means for enabling optional parsing of a selected part of said notes by selection of a text segment within said single text pane.

28. The system of claim 20, wherein the transaction parser-coder includes means to resolve instances of non-specification of genre and/or missing joiner attributes by parsing given semiotic form one input to infer and automatically insert missing genre and attributes to provide preemptive estimation of guess user intent.

29. The system of claim 20, configured for input of a semiotic form one text passage encapsulating multiple medical transactions comprising an entire medical consultation, said text passage demarcated into sentences by demarcation signifiers, the transaction parser-coder configured to parse the passage sentence by sentence.

30. The system of claim 20 for use with medical transactions concerning a patient's symptoms and signs, the transaction parser-coder including means to code for a related context of each transaction, the context based on implied or input contextual keywords, thereby enabling cognitive services to effect machine decision support.

31. The system of claim 20, wherein the transaction parser-coder is configured to provide decision support by auto-generating transaction codes representing recommended medical transactions in response to input transactions.

32. The system of claim 20, including means for modulating the transaction parser-coder in accordance with historical use of semiotic form one input by a user or the historical use of semiotic form one in the medical record of a particular patient.

33. A computer-based method of recording medical transactions through de novo composition and construction of medical transaction codes; including the steps of:
   inputting medical transactions in a semiotic form one, the semiotic form one input being a free form-type, abbreviation-oriented natural language textual input, parsing said semiotic form one input and converting it into coded medical transactions, wherein each transaction includes a unique patient identifier categorised under a linnean classification system, the unique patient identifier being human readable and comprehensible, in a semiotic form two output, the transaction codes composed and constructed de novo, the semiotic form two output embodying high level machine-parseable computer language statements comprehensible to a high certainty level by human users, causing a user display to display system reflection in the form of coded medical transactions in said semiotic form two and system-rated confidence levels representing the match between a code and correspondence with perceived user intent, receiving user selection input for verifying a selected coded medical transaction, converting a semiotic form two input into a semiotic form three transaction by mapping the selected coded transaction into data row in a relational database to render the transaction data amenable to structured query language processing.

34. The method of claim 33, wherein the unique patient identifier comprises a concatenated expression of its membership of the poly-genera of computed date of birth, sex, names of patient and forebears, and locality at a given point in time.

* * * * *